(12) United States Patent
Hilger et al.

(10) Patent No.: US 6,872,381 B1
(45) Date of Patent: Mar. 29, 2005

(54) RADIOPHARMACEUTICALS FOR DIAGNOSING ALZHEIMER'S DISEASE

(75) Inventors: Christoph-Stephan Hilger, Berlin (DE); Bernd Johannsen, Dresden (DE); Joerg Steinbach, Bischofswerda (DE); Peter Maeding, Dresden (DE); Meredith Halks-Miller, Woodside, CA (US); Richard Horuk, Lafayette, CA (US); Harald Dinter, San Rafael, CA (US); Raju Mohan, Moraga, CA (US); Joseph E. Hesselgesser, San Francisco, CA (US)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/626,725

(22) Filed: Jul. 25, 2003

Related U.S. Application Data

(63) Continuation of application No. 09/985,938, filed on Nov. 6, 2001, now Pat. No. 6,676,926.
(60) Provisional application No. 60/246,299, filed on Nov. 6, 2000.

(51) Int. Cl.$^7$ ................................................ A61K 49/04
(52) U.S. Cl. ...................... 424/9.4; 424/1.11; 424/1.81; 424/1.85; 424/9.1; 424/9.1; 424/1.89
(58) Field of Search ................................ 424/1.11, 1.65, 424/1.81, 1.89, 9.1, 9.4, 1.85; 544/224, 238

(56) References Cited

U.S. PATENT DOCUMENTS

| | | |
|---|---|---|
| 5,286,728 A | 2/1994 | Ferrini |
| 5,358,712 A | 10/1994 | Efange et al. |
| 5,721,243 A | 2/1998 | Efange et al. |
| 5,919,797 A | 7/1999 | Goodman et al. |
| 6,207,665 B1 | 3/2001 | Bauman et al. |
| 6,676,926 B2 * | 1/2004 | Hilger et al. ............... 424/9.1 |

FOREIGN PATENT DOCUMENTS

| | | |
|---|---|---|
| FR | 2 758 328 A1 | 7/1998 |
| WO | WO 92/16239 A1 | 10/1992 |
| WO | WO 96/01656 A1 | 1/1996 |
| WO | WO 98/02151 A2 | 1/1998 |
| WO | WO 99/51594 A1 | 10/1999 |
| WO | WO 00/14086 A1 | 3/2000 |
| WO | WO 00/42011 A1 | 7/2000 |
| WO | WO 00/58305 A1 | 10/2000 |

OTHER PUBLICATIONS

K. Bergström et al., "Iodine–123 labelled Z–(R,R)–IQNP: a potential radioligand for visualization of $M_1$ and $M_2$ muscarinic acetylcholine receptors in Alzheimer's disease", European Journal of Nuclear Medicine, vol. 26, No. 11, pp. 1482–1485, Nov. 1999, XP–002193046.

S. Oya et al., "Small and neutral Tc'O.BAT, bisaminoethanethiol ($N_2S_2$) complexes for developing new brain imaging agents", Nuclear Medicine & Biology, vol. 25, pp. 35–140, 1998.

A. Fischman et al., "Rapid detection of parkinson's disease by SPECT with altropane: A selective ligand for dopamine transporters", SYNAPSE, vol. 29, pp. 128–141, 1998.

J. Logan et al., "Graphical analysis of reversible radioligand binding from time–activity measurements applied to [N–$^{11}$C–methyl]–(–)–cocaine PET studies in human subjects", Journal of Cerebral Blood Flow and metabolism, vol. 10, pp. 740–747, 1990.

J. Seibyl et al., "Iodine–123–β–CIT an diodine–123–FPCIT SPECT measurement of dopamine transporter in healthy subjects and parkinson's patients", The Journal of Nuclear Medicine, vol. 39, No. 9, pp. 1500–1508, Sep. 1998.

M. Melloul et al., "Double–Phase $^{99m}$Tc–sestamibi scintimammography and trans–scan in diagnosing breast cancer", The Journal Of Nuclear Medicine, vol. 40, No. 3, pp. 380, Mar. 1999.

J.L. Moretti et al., "Comparison of brain SPECT using $^{99m}$Tc–Bicisate (L,L–ECD) and [$^{123}$I]IMP in cortical and subcortical strokes", Journal Of Cerebral Blood Flow And Metabolism, vol. 14 (Suppl. 1), pp. S84–S90, 1994.

J.M. Links, "Visual Interpretation," Chapter 22 in HN Wagner et al. (Eds.), Principles of Nuclear Medicine, W.B. Saunders Company, 2$^{nd}$ Edition, 1995, pp. 391–392.

EL Palmer et al. (Eds.), Practical Nuclear Medicine, Chapter 3 "Cardiovascular Imaging," W.B. Saunders Company, 1992, pp. 71–120.

* cited by examiner

Primary Examiner—Dameron L. Jones
(74) Attorney, Agent, or Firm—Millen, White, Zelano, Branigan, P.C.

(57) ABSTRACT

This invention is directed to the use of radiopharmaceuticals in diagnosing Alzheimer's disease. In particular the radiopharmaceuticals of the invention are able to pass through the blood-brain barrier and bind to the CCR1 receptor present in brain tissue of patients having Alzheimer's disease.

30 Claims, 10 Drawing Sheets

CCR1 and Amyloid 1-42 in the Entorhinal Cortex

Congophilic Angiopathy

Multi-Infarct Dementia

Diffuse Lewy Body Dementia

Parkinsonian Dementia of Guam

Pick's Disease

Progressive Supranuclear Palsy

RADIOPHARMACEUTICALS FOR DIAGNOSING ALZHEIMER'S DISEASE

This application is a continuation of Ser. No. 09/985,938 filed Nov 6, 2001 now U.S. Pat. No. 6,676,926 which claims benefit of U.S. Provisional Application Ser. No. 60/246,299, filed Nov. 6, 2000, the disclosure of which is hereby incorporated by reference.

FIELD OF THE INVENTION

The present invention relates to novel radiopharmaceuticals useful for the diagnosis of Alzheimer's disease.

BRIEF DESCRIPTION OF THE BACKGROUND ART

Alzheimer's disease is a severe neurodegenerative disorder, and currently about 4 million Americans suffer from this disease. As the aging population continues to grow, this number could reach 14 million by the middle of next century unless a cure or prevention is found. At present, there is no sensitive and specific premortem test for early diagnosis of this disease. Alzheimer's disease is currently diagnosed based on the clinical observation of cognitive decline, coupled with the systematic elimination of other possible causes of those symptoms. The confirmation of the clinical diagnosis of "probable Alzheimer's disease" can only be made by examination of the postmortem brain. The Alzheimer's disease brain is characterized by the appearance of two distinct abnormal proteinaceous deposits in regions of the brain responsible for learning and memory (e.g., cerebral cortex and hippocampus). These deposits are extracellular amyloid plaques, which are characteristic of Alzheimer's disease, and intracellular neurofibillary tangles (NFTs), which can be found in other neurodegenerative disorders as well. Amyloid peptides are typically either 40 or 42 amino acids in length ("$A\beta^{1-40}$" or "$A\beta^{1-42}$", respectively) and are formed from abnormal processing of a larger membrane-associated protein of unknown function, the amyloid precurser protein ("APP"). Oligomeric aggregates of these peptides are thought to be neurotoxic, eventually resulting in synaptic degeneration and neuronal loss. The amount of amyloid deposition roughly correlates with the severity of symptoms at the time of death.

In the past, there have been several attempts for the design of radiopharmaceuticals that could be used as diagnostic agents for a premortem diagnosis of Alzheimer's disease.

Bomebroek et al. showed that the amyloid-associated protein serum amyloid P component (SAP), labeled with $^{123}$I, accumulates at low levels in the cerebral cortex, possibly in vessel walls, of patients with cerebral amyloidosis (Bomebroek, M., et al., *Nucl. Med. Commun.* (1996), Vol. 17, pp. 929–933).

Saito et al. proposed a vector-mediated delivery of $^{125}$I-labeled $A\beta^{1-40}$ through the blood-brain barrier. It is reported that the iodinated $A\beta^{1-40}$ binds $A\beta$ amyloid plaque in tissue sections (Saito, Y., et al., *Proc. Natl. Acad. Sci. USA* 1995, Vol. 92, pp. 10227–10231).

U.S. Pat. No. 5,231,000 discloses antibodies with specificity to A4 amyloid polypeptide found in the brain of Alzheimer's disease patients. However, a method to deliver these antibodies across the blood-brain barrier has not been described.

Zhen et al. described modifications of the amyloid-binding dye known as "Congo Red™", and complexes of these modified molecules with technetium and rhenium. The complexes with radioactive ions are purported to be potential imaging agents for Alzheimer's disease (Zhen et al., *J. Med. Chem.*(1999), Vol. 42, pp. 2805–2815). However, the potential of the complexes to cross the blood-brain barrier is limited.

A group at the University of Pennsylvania in the U.S.A. (Skovronsky, M., et al., *Proc. Natl. Acad. Sci.* 2000, Vol. 97, pp. 7609–7614) has developed a fluorescently labeled derivative of Congo Red that is brain permeable and that non-specifically binds to amyloid materials (that is, peptides in β-pleated sheet conformation). This compound would need to be radiolabeled and then run through pre-clinical screens for pharmacokinetics and toxicity before clinical testing.

Klunk et al. reported experiments with a derivative of Congo Red™, Chrysamine G (CG). It is reported that CG binds synthetic β-amyloid well in vitro, and crosses the blood-brain barrier in normal mice (Klunk et al., *Neurobiol. Aging* (1994), Vol. 15, No. 6, pp. 691–698).

Bergström et al. presented a compound labeled with iodine-123 as a potential radioligand for visualization of $M_1$ and $M_2$ muscarinic acetylcholine receptors in Alzheimer's disease (Bergström et al., *Eur. J. Nucl. Med.* (1999), Vol. 26, pp. 1482–1485).

Recently, it has been discovered that certain specific chemokine receptors are upregulated in the brains of patients with Alzheimer's disease (Horuk, R. et al., *J. Immunol.* (1997), Vol. 158, pp. 2882–2890); Xia et al., *J. NeuroVirol.* (1999), Vol. 5, pp. 32–41). In addition, it has been shown recently that the chemokine receptor CCR1 is upregulated in the brains of patients with advanced Alzheimer's disease and absent in normal-aged brains (Halks-Miller et al, *CCR1 Immunoreactiviy in Alzheimer's Disease Brains*, Society for Neuroscience Meeting Abstract, #787.6, Volume 24, 1998). Antagonists to the CCR1 receptor and their use as anti-inflammatory agents are described in the PCT Published Patent Application, WO 98/56771.

None of the above described proposals have resulted in a clinical development of an imaging agent for the early diagnosis of Alzheimer's disease. Accordingly, there is still a clinical need for a diagnostic agent that could be used for a reliable and early diagnosis of Alzheimer's disease.

SUMMARY OF THE INVENTION

The present invention is directed to radiopharmaceuticals that bind to the CCR1 receptor and are able to pass through the blood-brain barrier, and are therefore useful in diagnosing Alzheimer's disease, preferably at an early stage of the disease.

Accordingly, in one aspect, the invention is directed to compounds of formula (I):

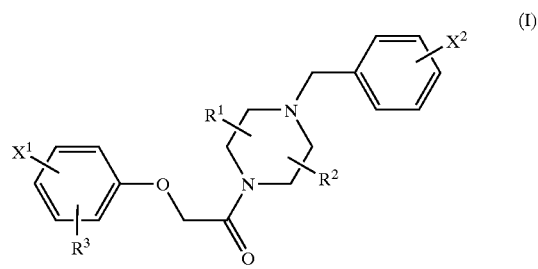

wherein:
$X^1$ and $X^2$ are each independently halo;

$R^1$ and $R^2$ are each independently hydrogen or alkyl; and
$R^3$ is hydrogen, amino, monoalkylamino, dialkylamino, monoaralkylamino, alkylcarbonylamino, alkenylcarbonylamino, haloalkylcarbonylamino, arylcarbonylamino, alkoxyalkylcarbonylamino, alkoxycarbonylalkylcarbonylamino, glycinamido, monoalkylglycinamido, arylcarbonylglycinamido, aminocarbonylglycinamido, (aminocarbonyl)(alkyl)glycinamido, (alkoxyalkylcarbonyl)glycinamido, ureido, monoalkylureido, monoarylureido, monoaralkylureido, or alaninamido;

and wherein either one of $X^1$ or $X^2$ is selected from the group of $^{123}I$, $^{125}I$, $^{128}I$, $^{131}I$, $^{75}Br$, $^{76}Br$, $^{80}Br$ and $^{18}F$; or wherein one of the carbon atoms in the compound is $^{11}C$;

or a pharmaceutically acceptable salt thereof.

In another aspect, the invention is directed to compounds of formula (II):

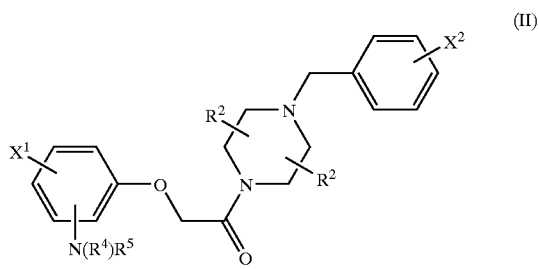

(II)

wherein
$X^1$ and $X^2$ are each independently halo;
$R^1$ and $R^2$ are each independently hydrogen or alkyl; and
$R^4$ is hydrogen; and
$R^5$ comprises a chelator capable of binding a radioactive metal atom chosen from the group of $^{99m}Tc$, $^{186}Re$ and $^{188}Re$;

or as a complex with $^{99m}Tc$, $^{186}Re$ and $^{188}Re$;
or a pharmaceutically acceptable salt thereof.

In another aspect, this invention is directed to a method of diagnosing Alzheimer's disease in a human which comprises administering to a human in need of such diagnosis compound of formula (I) or formula (II), as described above and herein, and measuring the radioactivity arising from the administration of the compound to the human either by using a gamma camera or by positron emission tomography (PET).

In another aspect, the invention is directed to a method of using a compound of the invention for the manufacture of a radiopharmaceutical for the diagnosis of Alzheimer's disease in a human.

In another aspect, the invention is directed to a method of preparing compounds of the invention.

Upon further study of the specification and appended claims, further objects and advantages of this invention will become apparent to those skilled in the art.

BRIEF DESCRIPTION OF THE FIGURES

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE INVENTION

Definitions

Figure 1:
FIG. 1 shows the expression of CCR1 in Alzheimer's disease brain tissue.

As used in the specification and appended claims, unless specified to the contrary, the following terms have the meaning indicated:

"Alkyl" refers to a straight or branched chain monovalent or divalent radical consisting solely of carbon and hydrogen, containing no unsaturation and having from one to eight carbon atoms, e.g., methyl, ethyl, n-propyl, 1-methylethyl (iso-propyl), n-butyl, n-pentyl, 1,1-dimethylethyl (t-butyl), n-heptyl, and the like.

"Alkylcarbonylamino" refers to a radical of the formula —N(H)—C(O)—$R_a$ where $R_a$ is an alkyl radical as defined above, e.g., acetylamino, ethylcarbonylamino, n-propylcarbonylamino, and the like.

"Alkenyl" refers to a straight or branched chain monovalent or divalent radical consisting solely of carbon and hydrogen, containing at least one double bond and having from two to eight carbon atoms, e.g., ethenyl, prop-1-enyl, but-1-enyl, pent-1-enyl, penta-1,4-dienyl, and the like.

"Alkenylcarbonylamino" refers to a radical of the formula —N(H)—C(O)—$R_c$ where $R_c$ is an alkenyl radical as defined above, e.g., ethenylcarbonylamino, prop-2-enylcarbonylamino, but-2-enylcarbonylamino, and the like.

"Alkoxy" refers to a radical of the formula —O$R_a$ where $R_a$ is an alkyl radical as defined above, e.g., methoxy, ethoxy, n-propoxy, 1-methylethoxy (iso-propoxy, n-butoxy, n-pentoxy, 1,1-dimethylethoxy (t-butoxy), and the like.

"Alkoxycarbonylalkylcarbonylamino" refers to a radical of the formula —N(H)—C(O)—$R_a$—C(O)O$R_a$ where each $R_a$ is independently an alkyl radical as defined above, e.g., ethoxycarbonylmethylcarbonylamino, methoxycarbonylmethylcarbonylamino, (2-ethoxycarbonylethyl) carbonylamino, (2-methoxycarbonylethyl)carbonylamino, and the like.

"(Alkoxyalkylcarbonyl)glycinamido" refers to a radical of the formula —N(H)(O)—$CH_2$—N(H)(O)—$R_a$—O—$R_a$ where each $R_a$ is independently an alkyl radical as defined above, e.g., (methoxyacetyl)glycinamido, (ethoxyacetyl) glycinamido, and the like.

"Amino" refers to the radical —$NH_2$.

"Aminocarbonylglycinamido" refers to a radical of the formula —N(H)C(O)—$CH_2$—N(H)—C(O)—$NH_2$.

"(Aminocarbonyl)(alkyl)glycinamido" refers to a radical of the formula —N(H)—C(O)—$CH_2$—N($R_a$)—C(O)—$NH_2$ where $R_a$ is an alkyl radical as defined above.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of halo, alkyl, alkoxy, haloalkyl, haloalkoxy, nitro, amino, monoalkylamino, and dialkylamino, as defined herein.

"Arylcarbonylamino" refers to a radical of the formula —N(H)—C(O)—$R_b$ where $R_b$ is an aryl radical as defined above, e.g., (4-methoxyphenyl)carbonylamino, (4-fluorophenyl)carbonylamino, (4-chlorophenyl) carbonylamino, and the like.

"Arylcarbonylglycinamido" refers to a radical of the formula —N(H)—C(O)—CH$_2$—N(H)—C(O)—$R_b$ where $R_b$ is an aryl radical as defined above, e.g., phenylcarbonylglycinamido, (4-fluoro-3-trifluoromethyl-phenyl)carbonylglycinamido, (4-fluorophenyl) carbonylglycinamido, and the like.

"Aralkyl" refers to a radical of the formula—$R_a R_b$ where $R_a$ is an alkyl radical as defined above and $R_b$ is an aryl radical as defined above, e.g., benzyl, and the like.

"Alkoxyalkylcarbonylamino" refers to a radical of the formula —N(H)—C(O)—$R_a$—O—$R_a$ where each $R_a$ is an alkyl radical as defined above, e.g., methoxymethylcarbonylamino, ethoxyethylcarbonylamino, methoxyethylcarbonylamino, and the like.

"Alaninamido" refers to a radical of the formula —N(H)—C(O)—C(CH$_3$)H—NH$_2$.

"Benzyl" refers to a radical of the formula —CH$_2$—$R_h$ where $R_h$ is a phenyl radical optionally substituted by one or more substituents selected from the group consisting of halo, alkyl, haloalkyl, alkoxy, nitro, amino, monoalkylamino, and dialkylamino.

"Dialkylamino" refers to a radical of the formula —N($R_a$)$R_a$ where each $R_a$ is independently an alkyl radical as defined above, e.g., dimethylamino, methylethylamino, diethylamino, dipropylamino, ethylpropylamino, and the like.

"Glycinamido" refers to a radical of the formula —N(H)—C(O)—CH$_2$—NH$_2$.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2-trifluoroethyl, 1-fluoromethyl-2-fluoroethyl, 3-bromo-2-fluoropropyl, 1-bromomethyl-2-bromoethyl, and the like.

"Haloalkylcarbonylamino" refers to a radical of the formula —N(H)(O)—$R_f$ where $R_f$ is an haloalkyl radical as defined above, e.g., trifluoromethylcarbonylamino, trifluoromethylcarbonylamino, 2-bromoethylcarbonylamino, and the like.

"Monoalkylamino" refers to a radical of the formula —N(H)$R_a$ where $R_a$ is an alkyl radical as defined above, e.g., methylamino, ethylamino, propylamino, and the like.

"Monoaralkylamino" refers to a radical of the formula —N(H)$R_d$ where $R_d$ is an aralkyl radical as defined above, e.g., benzylamino, (3,4,5-trimethoxybenzyl)amino, (4-chlorobenzyl)amino, and the like.

"Monoalkylglycinamido" refers to a radical of the formula —N(H)—C(O)—CH$_2$—N(H)$R_a$ where $R_a$ is an alkyl radical as defined above.

"Monoalkylureido" refers to a radical of the formula —N(H)—C(O)—N(H)$R_a$ or a radical of the formula —N($R_a$)—C(O)—NH$_2$ where $R_a$ is an alkyl radical as defined above.

"Monoarylureido" refers to a radical of the formula —N(H)—C(O)N(H)Rb or a radical of the formula —N($R_b$)—C(O)—NH$_2$ where $R_b$ is an aryl radical as defined above.

"Monoaralkylureido" refers to a radical of the formula —N(H)—C(O)—N(H)$R_d$ or a radical of the formula —N($R_d$)—C(O)—NH$_2$ where $R_d$ is an aralkyl radical as defined above.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like. Particularly preferred salts of compounds of the invention are the monochloride salts and the dichloride salts.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Ureido" refers to a radical of the formula —N(H)—C(O)—NH$_2$.

It is understood from the above definitions and examples that for radicals containing a substituted alkyl group any substitution thereon can occur on any carbon of the alkyl group.

The compounds of the invention, or their pharmaceutically acceptable salts, may have asymmetric carbon atoms in their structure. The compounds of the invention and their pharmaceutically acceptable salts may therefore exist as single enantiomers, diastereoisomers, racemates, and mixtures of enantiomers and diastereomers. All such single enantiomers, diastereoisomers, racemates and mixtures thereof are intended to be within the scope of this invention. Absolute configuration of certain carbon atoms within the compounds, if known, are indicated by the appropriate absolute descriptor R or S.

Separate enantiomers can be prepared through the use of optically active starting materials and/or intermediates or through the use of conventional resolution techniques, e.g., enzymatic resolution or chiral HPLC.

Utility and Administration

The compounds of the invention as described herein are antagonists to the chemokine receptor known as CCR1 and have the ability to pass the blood-brain barrier. The compounds are therefore suited as in vivo diagnostic agents for imaging of Alzheimer's disease. The detection of radioactivity is performed according to well-known procedures in the art, either by using a gamma camera or by positron emission tomography (PET).

Preferably, the free base or a pharmaceutically acceptable salt form, e.g. a monochloride or dichloride salt, of a compound of the invention is used in a galenical formulation as diagnostic agent. The galenical formulation containing the compound of the invention optionally contains adjuvants known in the art, e.g. buffers, sodium chloride, lactic acid, surfactants etc. A sterilization by filtration of the galenical formulation under sterile conditions prior to usage is possible.

The radioactive dose should be in the range of 1 to 100 mCi, preferably 5 to 30 mCi, and most preferably 5 to 20 mCi per application.

Testing

The suitability of the compounds as imaging agents for Alzheimer's disease can be demonstrated by experimental protocols known to those of ordinary skill in the art. For example, the upregulation of CCR1 receptors in Alzheimer's disease brains can be demonstrated in immunohistochemical staining experiments of autopsy brain tissue collected from Alzheimer's disease patients as described in detail below in the Examples. The ability of the compounds of the invention to bind to the CCR1 receptor and their ability to pass through the blood-brain barrier, can also be assessed in known in vitro and in vivo assays as described below in the Examples. In particular, Example 10 describes a large study that was undertaken to address the degree of CCR1 expression in different stages of Alzheimer's disease. Brain tissue from 50 autopsy cases showed a correlation between degree of clinical severity (dementia) in Alzheimer's disease and CCR1 expression in dystrophic neurites. CCR1 expression in plaque-like structures within the brains of clinically normal individuals is rare. Also, CCR1 expression is not found in the brains of individuals with other neurodegenerative diseases unless there is a concomitant Alzheimer's disease pathology (specifically, $A\beta^{1-42}$ in plaques).

Preferred Embodiments

Of the various aspects of the invention, certain compounds of formula (I) are preferred. In particular, compounds of formula (1) wherein $X^1$ is a chloro at the 4-position of the phenyl ring and $X^2$ is a $^{18}F$ atom at the 4-position of the phenyl ring are preferred. Especially preferred are such compounds for use as diagnostic agents in positron emission tomography (PET).

Even more preferred are those compounds of formula (I) wherein $R^3$ is in the 2-position of the phenyl ring and $R^1$ is a methyl at the 2-position of the piperazinyl ring and $R^2$ is a methyl at the 5-position of the piperazinyl ring. Equally preferred are those compounds of formula (I) wherein $R^3$ is in the 2-position of the phenyl ring and $R^1$ is a methyl in the 2-position of the piperazinyl ring and $R^2$ is hydrogen.

Further preferred are these preferred compounds in their mono- or dichloride salt form.

Of the various aspects of the invention, certain compounds of formula (II) are preferred. In particular, compounds of formula (II) wherein —$N(R^4)R^5$ is in the 2-position of the phenyl ring and $R^1$ is in the 2-position of the piperazinyl ring and $R^2$ is in the 5-position of the piperazinyl ring. Equally preferred are those compounds of formula (II) wherein —$N(R^4)R^5$ is in the 2-position of the phenyl ring and $R^2$ is a methyl in the 2-position of the piperazinyl ring and $R^2$ is hydrogen.

Even more preferred are those compounds of formula (II) wherein $R^5$ comprises a chelator according to formula (III):

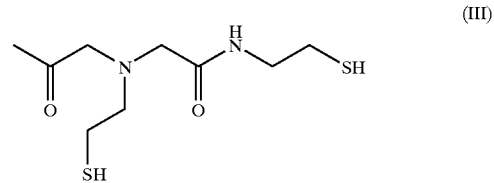

(III)

or formula (IV):

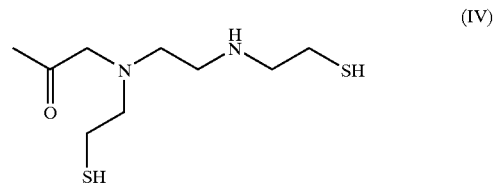

(IV)

as well as their complexes with $^{99m}Tc$, $^{186}Re$ and $^{188}Re$. Of these preferred compounds, even more preferred are those compounds of formula (II) wherein $R^5$ comprises a chelator according to formula (III) or (IV), and wherein the chelator is bound to the nitrogen in the —$N(R^4)R^5$ group of the non-radioactive compound of formula (II) via a linker moiety comprising an alkyl radical having one to ten carbon atoms, wherein the alkyl radical optionally contains one to ten —C(O)-groups, one to ten —C(O)N(R)-groups, one to ten —N(R)C(O)-groups, one to ten —N(R)-groups, one to ten —N(R)$_2$ groups, one to ten hydroxy groups, one to ten —C(O)OR— groups, one to ten oxygen atoms, one to ten sulfur atoms, one to ten nitrogen atoms, one to ten halogen atoms, one to ten aryl groups, and one to ten saturated or unsaturated heterocyclic rings wherein R is hydrogen or alkyl. For example, the linker moiety can be an alkyl radical having 1 to 10 carbon atoms, wherein one or more $CH_2$ groups is optionally replaced by, in each case independently, —C—, —S—, —N(R)—, —C(O)—, —C(O)N(—R)— or N(R)C(O)— groups. This alkyl radical can also be optionally substituted by one or more —N(R)$_2$ groups, hydroxy groups, —C(O)OR groups, or halogen atoms, wherein R is hydrogen or alkyl. A preferred linker moiety is —C(O)—$CH_2N(H)$—.

Of the compounds of the invention, the most preferred compounds of formula (I) are those compounds selected from the group consisting of the following:

1-(5-chloro-2-{2-[(2R)-4-(4-fluoro-$^{18}F$-benzyl)-2-methylpiperazin-1-yl]-2-oxoethoxy}phenyl)urea;

N'-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide, technetium-99m-complex;

1-(2-{2-[(2R)-4-(4-fluorobenzyl)-2-methylpiperazin-1-yl]-2-oxoethoxy}-5-iodo-$^{123}I$-phenyl)urea;

N'-(2-mercaptoeth-1-yl)-N'(5-mercapto-3-aza-2-oxopent-1-yl)-N-{5-chloro-2-[2-[4-(4-fluorobenzyl)-2-(2R)- methylpiperazin-1-yl]-2-oxoethoxy]phen-1-yl}glycinamide, technetium-99m-complex;
N'-(2-mercaptoeth-1-yl)-N'-(5-mercapto-3-azapent-1-yl)-N-{5-chloro-2-[2-[4-(4-fluorobenzyl)-2-(2R)-methylpiperazin-1-yl]-2-oxoethoxy]phen-1-yl}glycinamide, technetium-99m-complex;
2-(2-amino-4-chlorophenoxy)-1-[(2SR,5RS)-4-(4-fluoro-$^{18}$F-benzyl)-2,5-dimethylpiperazin-1-yl]ethan-1-one;
2-(2-amino-4-chlorophenoxy)-1-[(2RS,5RS)-4-(4-fluoro-$^{18}$F-benzyl)-2,5-dimethylpiperazin-1-yl]ethan-1-one;
2-(2-amino-4-chlorophenoxy)-1-[(2SR,5SR)-4-(4-fluoro-$^{18}$F-benzyl)-2,5-dimethylpiperazin-1-yl]ethan-1-one;
2-(2-amino-4-chlorophenoxy)-1-((2RS,5SR)-4-(4-fluoro-$^{18}$F-benzyl)-2,5-dimethylpiperazin-1-yl]ethan-1-one;
2-[4-chloro-2-(diethyramino)phenoxy]-1-[(2SR,5RS)-4-(4-fluoro-$^{18}$F-benzyl)-2,5-dimethylpiperazin-1-yl]ethan-1-one;
2-[4-chloro-2-(diethylamino)phenoxy]-1-[(2RS,5RS)-4-(4-fluoro-$^{18}$F-benzyl)-2,5-dimethylpiperazin-1-yl]ethan-1-one;
2-[4-chloro-2-(diethylamino)phenoxy]-1-[(2SR,5SR)-4-(4-fluoro-$^{18}$F-benzyl)-2,5-dimethylpiperazin-1-yl]ethan-1-one;
2-[4-chloro-2-(diethylamino)phenoxy]-1-[(2RS,5SR)-4-(4-fluoro-$^{18}$F-benzyl)-2,5-dimethylpiperazin-1-yl]ethan-1-one;
1-(5-chloro-2-{2-[(2RS,5SR)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2SR,5SR)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2SR,5RS)-4-(4-fluoro-$^{18}$F-benzyl)-2,5-dimethylpiperazin-1-yl]-2-oxoethoxy}phenyl)-3(2,4-dichlorophenyl)urea;
1-(5-chloro-2-{2-[(2RS,5SR)-4-(4-fluoro-$^{18}$F-benzyl)-2,5-dimethylpiperazin-1-yl]-2-oxoethoxy}phenyl)urea;
1-(5-chloro-2-{2-[(2SR,5SR)-4-(4-fluoro-$^{18}$F-benzyl)-2,5-dimethylpiperazin-1-yl]-2-oxoethoxy}phenyl)urea;
1-(5-chloro-2-{(2-[(2RS,5RS)-4-(4-fluoro-$^{18}$F-benzyl)-2,5-dimethylpiperazin-1-yl]-2-oxoethoxy}phenyl)urea;
1-(5-chloro-2-{2-[(2SR,5RS)-4-(4-fluoro-$^{18}$F-benzyl)-2,5-dimethylpiperazin-1-yl]2-oxoethoxy}phenyl)urea;
1-(5-chloro-2-{2-[(2RS,5SR)-4-(4-fluoro-$^{18}$F-benzyl)-2,5-dimethylpiperazin-1-yl]-2-oxoethoxy}phenyl)urea;
1(5-chloro-2-{2-[(2SR,5SR)-4-(4-fluoro-$^{18}$F-benzyl)-2,5-dimethylpiperazin-1-yl]-2-oxoethoxy}phenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)urea;
1-(5-chloro-2-{2-[(2SR,5RS)-4-(4-fluoro-$^{18}$F-benzyl)-2,5-dimethylpiperazin-1-yl]-2-oxoethoxy}phenyl)urea;
1-[(2SR,5RS)-4-(4-fluoro-$^{18}$F-benzyl)-2,5-dimethylpiperazin-1-yl]-2-(2-isopentylamino-4-chlorophenoxy)ethan-1-one;
1-[(2RS,5RS)-4-(4-fluoro-$^{18}$F-benzyl)-2,5-dimethylpiperazin-1-yl]-2-(2-isopentylamino-4-chlorophenoxy)ethan-1-one;
1-[(2SR,5SR)-4-(4-fluoro-$^{18}$F-benzyl)-2,5-dimethylpiperazin-1-yl]-2-(2-isopentylamino-4-chlorophenoxy)ethan-1-one;
1-[(2RS,5SR)-4-(4-fluoro-$^{18}$F-benzyl)-2,5-dimethylpiperazin-1-yl]-2-(2-isopentylamino-4-chlorophenoxy)ethan-1-one;
N-(5-chloro-2-{2-[(2SR,5RS)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2RS,5RS)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2SR,5SR)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-methylpropanamide;
N-(5 chloro-2-{2-[(2SR,5RS)-4-(4-fluoro-$^{18}$F-benzyl)-2,5-dimethylpiperazin-1-yl]-2-oxoethoxy}phenyl)-2-(methoxy)acetamide;
N-(5-chloro-2-{2-[(2RS,5RS)-4-(4-fluoro-$^{18}$F-benzyl)-2,5-dimethylpiperazin-1-yl]-2-oxoethoxy}phenyl)-2-(methoxy)acetamide;
N-(5-chloro-2-{2-[(2SR,5SR)-4-(fluoro-$^{18}$F-benzyl)-2,5-dimethylpiperazin-1-yl]-2-oxoethoxy}phenyl)-2-(methoxy)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(methoxy)acetamide;
(E)-N-5-chloro-2-{2-[(2RS,5SR)-4-(4-fluoro-$^{18}$F-benzyl)-2,5-dimethylpiperazin-1-yl]-2-oxoethoxy}phenyl)-2-butenamide;
(E)-N-(5-chloro-2-{2-[(2SR,5SR)-4-(4-fluoro-$^{18}$F-benzyl)-2,5-dimethylpiperazin-1-yl]-2-oxoethoxy}phenyl)-2-butenamide;
(E)-N-5-chloro-2-{2-[(2SR,5RS)-4-(4-fluoro-$^{18}$F-benzyl)-2,5-dimethylpiperazin-1-yl]-2-oxoethoxy}phenyl)-2-butenamide;
(E)-N-(5-chloro-2-{2-[(2SR,5RS)-4-(4-fluoro-$^{18}$F-benzyl)-2,5-dimethylpiperazin-1-yl]-2-oxoethoxy}phenyl)-2-butenamide;
methyl N-(5-chloro-2-{2-[(2SR,5RS)-4-(4-fluoro-$^{18}$F-benzyl)-2,5-dimethylpiperazin-1-yl]-2-oxoethoxy}phenyl)succinamate;
methyl N-(5-chloro-2-{2-[(2RS,5RS)-4-(4-fluoro-$^{18}$F-benzyl)-2,5-dimethylpiperazin-1-yl]-2-oxoethoxy}phenyl)succinamate;
methyl N-(5-chloro-2-{2-[(2SR,5SR)-4-(4-fluoro-$^{18}$F-benzyl)-2,5-dimethylpiperazin-1-yl]-2-oxoethoxy}phenyl)succinamate;
methyl N-(5-chloro-2-{2-[(2RS,5SR)-4-(4-fluoro-$^{18}$F-benzyl)-2,5-dimethylpiperazin-1-yl]-2-oxoethoxy}phenyl)succinamate;
ethyl N-(5-chloro-2-{2-[(2SR,5RS)-4-(4-fluoro-$^{18}$F-benzyl)-2,5-dimethylpiperazin-1-yl]-2-oxoethoxy}phenyl)succinamate;
ethyl N-(5-chloro-2-{2-[(2RS,5RS)-4-(4-fluoro-$^{18}$F-benzyl)-2,5-dimethylpiperazin-1-yl]-2-oxoethoxy}phenyl)succinamate; ethyl N-(5-chloro-2-{2-[(2SR,5SR)(4-fluoro-$^{18}$F-benzyl)-2,5-dimethylpiperazin-1-yl]-2-oxoethoxy}phenyl)succinamate;
ethyl N-(5-chloro-2-{2-[(2RS,5SR)-4-(4-fluoro-$^{18}$F-benzyl)-2,5-dimethylpiperazin-1-yl]-2-oxoethoxy}phenyl)succinamate;
N-(5-chloro-2-{2-(2SR,5RS)-4-(4-fluoro-$^{18}$F-benzyl)-2,5-dimethylpiperazin-1-yl]-2-oxoethoxy}phenyl)acetamide;
N-(5-chloro-2-{2-[(2RS,5RS)-4-(4-fluoro-$^{18}$F-benzyl)-2,5-dimethylpiperazin-1-yl]-2-oxoethoxy}phenyl)acetamide;
N-(5-chloro-2-{2-[(2SR,5SR)-4-(4-fluoro-$^{18}$F-benzyl)-2,5-dimethylpiperazin-1-yl]-2-oxoethoxy}phenyl)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)acetamide;
N-(5-chloro-2-{2-[(2SR,5RS)-4-(4-fluoro-$^{18}$F-benzyl)-2,5-dimethylpiperazin-1-yl]2-oxoethoxy}phenyl)propanamide;

N-(5-chloro-2-{2-[(2RS,5RS)-4-(4-fluoro-$^{18}$F-benzyl)-2,5-dimethylpiperazin-1-yl]-2-oxoethoxy}phenyl)propanamide;

N-(5-chloro-2-{2-[(2SR,5SR)-4-(4-fluoro-$^{18}$F-benzyl)-2,5-dimethylpiperazin-1-yl]-2-oxoethoxy}phenyl)propanamide;

N-(5-chloro-2-{2-((2RS,5SR)-4-(4-fluoro-$^{18}$F-benzyl)-2,5-dimethylpiperazin-1-yl]-2-oxoethoxy}phenyl)propanamide;

N-(5-chloro-2-{2-[(2SR,5RS)-4-(4-fluoro-$^{18}$F-benzyl)-2,5-dimethylpiperazin-1-yl]-2-oxoethoxy}phenyl)3-fluorobenzamide;

N-(5-chloro-2-{2-((2RS,5SR)-4-(4-fluoro-$^{18}$F-benzyl)-2,5-dimethylpiperazin-1-yl]-2-oxoethoxy}phenyl)-3-fluorobenzamide;

N-(5-chloro-2{-2-[(2SR,5SR)-4-(4-fluoro-$^{18}$F-benzyl)-2,5-dimethylpiperazin-1-yl]-2-oxoethoxy}phenyl)3-fluorobenzamide;

N-(5-chloro-2-{2-[(2RS,5RS)-4-(4-fluoro-$^{18}$F-benzyl)-2,5-dimethylpiperazin-1-yl]-2-oxoethoxy}phenyl)-3-fluorobenzamide;

1-(5-chloro-2-{2-[(2SR,5RS)-4-(4-fluoro-$^{18}$F-benzyl)-2,5-dimethylpiperazin-1-yl]-2-oxoethoxy}phenyl)3-(p-tolyl)urea;

1-(5-chloro-2-{2-[(2RS,5RS)-4(4-fluoro-$^{18}$F-benzyl)-2,5-dimethylpiperazin-1-yl]-2-oxoethoxy}phenyl)-3-(p-tolyl)urea;

1-(5-chloro-2-{2-[(2SR, 5SR)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2RS,5SR)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2RS,5SR)-4-(4fluoro-$^{18}$F-benzyl)-2,5-dimethylpiperazin-1-yl]-2-oxoethoxy}phenyl)-3-ethylurea;

1-(5-chloro-2-{2-[(2SR,5SR)-4-(4-fluoro-$^{18}$F-benzyl)-2,5-dimethylpiperazin-1-yl]-2-oxoethoxy}phenyl)-3-ethylurea;

1-(5-chloro-2-{2-[(2RS,5RS)4-(4-fluoro-$^{18}$F-benzyl)-2,5-dimethylpiperazin-1-yl]-2-oxoethoxy}phenyl)-3-ethylurea;

1-(5-chloro-2-{2[(2SR,5RS)-4-fluoro-$^{18}$F-benzyl)-2,5-dimethylpiperazin-1-yl]-2-oxoethoxy}phenyl)-3-ethylurea;

1-benzyl-3-(5-chloro-2-{2-[(2SR,5RS)-4-(4-fluoro-$^{18}$F-benzyl)-2,5-dimethylpiperazin-1-yl]-2-oxoethoxy}phenyl)urea;

1-benzyl-3-(5-chloro-2-{2-[(2RS,5RS)-4-(4-fluoro-$^{18}$F-benzyl)-2,5-dimethylpiperazin-1-yl]-2-oxoethoxy}phenyl)urea;

1-benzyl-3-(5-chloro-2-{2-[(2SR,5SR)-4-(4-fluoro-$^{18}$F-benzyl)-2,5-dimethylpiperazin-1-yl]-2-oxoethoxy}phenyl)urea;

1-benzyl-3-(5-chloro-2{2-[(2RS,5SR)-4-(4-fluoro-$^{18}$F-benzyl)-2,5-dimethylpiperazin-1-yl]-2-oxoethoxy}phenyl)urea;

1-(5-chloro-2-{2-[(2RS,5SR)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2SR,5SR)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2RS,5RS)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2SR,5RS)-4-(4-fluoro-$^{18}$F-benzyl)-2,5-dimethylpiperazin-1-yl]-2-oxoethoxy}phenyl)-3-(4-nitrophenyl)urea;

2-(2-benzylamino-4-chlorophenoxy)-1-[(2SR,5RS)-4-(4-fluoro-$^{18}$F-benzyl)2,5-dimethylpiperazin-1-yl]ethan-1-one;

2-(2-benzylamino-4-chlorophenoxy)-1-[(2RS,5RS)-4-(4-fluoro-$^{18}$F-benzyl)-2,5-dimethylpiperazin-1-yl]ethan-1-one;

2-(2-benzylamino-4-chlorophenoxy)-1-[(2SR,5SR)-4-(4-fluoro-$^{18}$F-benzyl)-2,5-dimethylpiperazin-1-yl]ethan-1-one;

2-(2-benzylamino-4-chlorophenoxy)-1-[(2RS,5SR)-4-(4-fluoro-$^{18}$F-benzyl)-2,5-dimethylpiperazin-1-yl]ethan-1-one;

N-(5-chloro-2-{2-[(2RS,5SR)-4-(4-fluoro-$^{18}$F-benzyl)-2,5-dimethylpiperazin-1-yl]-2-oxoethoxy}phenyl)glycinamide;

N-(5-chloro-2-{2-[(2SR,5RS)-4-(4-fluoro-$^{18}$F-benzyl)-2,5-dimethylpiperazin-1-yl]-2-oxoethoxy}phenyl)glycinamide;

N-(5-chloro-2-{2-[(2SR,5SR)-4-(4-fluoro-$^{18}$F-benzyl)-2,5-dimethylpiperazin-1-yl]2-oxoethoxy}phenyl)glycinamide;

N-(5-chloro-2-{2-[(2RS,5RS)-4-(4-fluoro-$^{18}$F-benzyl)-2,5-dimethylpiperazin-1-yl]-2-oxoethoxy}phenyl)glycinamide;

1-(5-chloro-2-{2-[(2R)-4-(4-fluoro-$^{18}$F-benzyl)-2-methylpiperazin-1-yl]-2-oxoethoxy}phenyl)urea;

1-(5-chloro-2-{2-[(2S)-4-(4-fluoro-$^{18}$F-benzyl)-2-methylpiperazin-1-yl]-2-oxoethoxy}phenyl)urea;

N-(5-chloro-2-{2-[(2RS,5SR)-4-(4-fluoro-$^{18}$F-benzyl)-2,5-dimethylpiperazin-1-yl]-2-oxoethoxy}phenyl)-2-(methylamino)acetamide;

N-(5-chloro-2-{2-[(2SR,5SR)-4-(4-fluoro-$^{18}$F-benzyl)-2,5-dimethyl-piperazin-1-yl]-2-oxoethoxy}phenyl)-2-(methylamino)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(methylamino)acetamide;

N-(5-chloro-2-{2-[(2SR,5RS)-4-(4-fluoro-$^{18}$F-benzyl)-2,5-dimethyl-piperazin-1-yl]-2-oxoethoxy}phenyl)-2-(methylamino)acetamide;

2-bromo-N-(5-chloro-2-{(2SR,5RS)-4-(4-fluoro-$^{18}$F-benzyl)-2,5-dimethylpiperazin-1-yl]-2-oxoethoxy}phenyl)acetamide;

2-bromo-N-(5-chloro-2-{(2RS,5RS)-4-(4-fluoro-$^{18}$F-benzyl)-2,5-dimethylpiperazin-1-yl]-2-oxoethoxy}phenyl)acetamide;

2-bromo-N-(5-chloro-2{(2SR,5SR)-4-(4-fluoro-$^{18}$F-benzyl)-2,5-dimethylpiperazin-1-yl]-2-oxoethoxy}phenyl)acetamide;

2-bromo-N-(5-chloro-2-{(2RS,5SR)-4-(4-fluoro-$^{18}$F-benzyl)-2,5-dimethylpiperazin-1-yl]-2-oxoethoxy}phenyl)acetamide;

N-(5-chloro-2-{2-[(2RS,5SR)4-(4-fluoro-$^{18}$F-benzyl)-2,5-dimethylpiperazin-1-yl]-2-oxoethoxy}phenyl)-2-(ureido)acetamide;

N-(5-chloro-2-{2-[(2SR,5SR)-4-(4-fluoro-$^{18}$F-benzyl)-2,5-dimethylpiperazin-1-yl]-2-oxoethoxy}phenyl)-2-(ureido)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(ureido)acetamide;

N-(5-chloro-2-{2-[(2SR,5RS)-4-(4-fluoro-$^{18}$F-benzyl)-2,5-dimethylpiperazin-1-yl]-2-oxoethoxy}phenyl)-2-(ureido)acetamide;

N-(5-chloro-2-{2-[(2RS,5SR)4(4-fluoro-$^{18}$F-benzyl)-2,5-dimethylpiperazin-1-yl]-2-oxoethoxy}phenyl)-2-(1-methylureido)acetamide;

N-(5-chloro-2-{2-[(2SR,5SR)4-(4-fluoro-$^{18}$F-benzyl)-2,5-dimethylpiperazin-1-yl]-2-oxoethoxy}phenyl)-2-(1-methylureido)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(1-methylureido)acetamide;

N-(5-chloro-2-{2-[(2SR,5RS)-4-(4-fluoro-$^{18}$F-benzyl)-2,5-dimethylpiperazin-1-yl]-2-oxoethoxy}phenyl)-2-(1-methylureido)acetamide;

(2RS)-N-(5-chloro-2-{2-[(2RS,5SR)-4-(4-fluoro-$^{18}$F-benzyl)-2,5-dimethylpiperazin-1-yl]-2-oxoethoxy}phenyl)-2-aminopropanamide;

(2SR)-N-(5-chloro-2-{2-[(2RS,5SR)-4-(4-fluoro-$^{18}$F-benzyl)-2,5-dimethylpiperazin-1-yl]-2-oxoethoxy}phenyl)-2-aminopropanamide;

(2RS)-N-(5-chloro-2-{2-[(2SR,5SR)-4-(4fluoro-$^{18}$F-benzyl)-2,5-dimethylpiperazin-1-yl]-2-oxoethoxy}phenyl)-2-aminopropanamide;

(2SR)-N-(5-chloro-2-{2-[(2SR,5SR)-4-(4-fluoro-$^{18}$F-benzyl)-2,5-dimethylpiperazin-1-yl]-2-oxoethoxy}phenyl)-2-aminopropanamide;

(2RS)-N-(5chloro-2-{2-[(2RS,5RS)-4-(4-fluoro-$^{18}$F-benzyl)-2,5-dimethylpiperazin-1-yl]-2-oxoethoxy}phenyl)-2-aminopropanamide;

(2SR)-N-(5-chloro-2-{2-[(2RS,5RS)-4-(4-fluoro-$^{18}$F-benzyl)-2,5-dimethylpiperazin-1-yl]-2-oxoethoxy}phenyl)-2-aminopropanamide;

(2RS)-N-(5-chloro-2-{2-[(2SR,5RS)-4-(4-fluoro-$^{18}$F-benzyl)-2,5-dimethylpiperazin-1-yl]-2-oxoethoxy}phenyl)-2-aminopropanamide;

(2SR)-N-(5-chloro-2-{2-[(2SR,5RS)-4-(4-fluoro-$^{18}$F-benzyl)-2,5-dimethylpiperazin-1-yl]-2-oxoethoxy}phenyl)-2-aminopropanamide;

N-(5-chloro-2-{2-[(2SR,5RS)-4-(4-fluoro-$^{18}$F-benzyl)-2,5-dimethylpiperazin-1-yl]-2-oxoethoxy}phenyl)-2-(2,4-difluorobenzoylamino)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(2,4-difluorobenzoylamino)acetamide;

N-(5-chloro-2-{2-[(2SR,5SR)-4-(4-fluoro-$^{18}$F-benzyl)-2,5-dimethylpiperazin-1-yl]-2-oxoethoxy}phenyl)-2-(2,4-difluorobenzoylamino)acetamide;

N-(5-chloro-2-{2-[(2RS,5SR)-4-(4-fluoro-$^{18}$F-benzyl)-2,5-dimethylpiperazin-1-yl]-2-oxoethoxy}phenyl)-2-(2,4-difluorobenzoylamino)acetamide;

N-(5-chloro-2-{2-[(2SR,5RS)-4-(4-fluoro-$^{18}$F-benzyl)-2,5-dimethylpiperazin-1-yl]-2-oxoethoxy}phenyl)-2-(methoxyacetylamino)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(methoxyacetylamino)acetamide;

N-(5-chloro-2-{2-[(2SR,5SR)-4-(4-fluoro-$^{18}$F-benzyl)-2,5-dimethylpiperazin-1-yl]-2-oxoethoxy}phenyl)-2-(methoxyacetylamino)acetamide;

N-(5-chloro-2-{2-[(2RS,5SR)-4-(4-fluoro-$^{18}$F-benzyl)-2,5-dimethylpiperazin-1-yl]-2-oxoethoxy}phenyl)-2-(methoxyacetylamino)acetamide;

N-(chloro-2-{2-[(2SR,5RS)-4-(4-fluoro-$^{18}$F-benzyl)-2,5-dimethylpiperazin-1-yl]-2 oxoethoxy}phenyl)-2-(2-iodobenzoylamino)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)-2-(2-iodobenzoylamino)acetamide;

N-(5-chloro-2-{2-[(2SR,5SR)-4-(4-fluoro-$^{18}$F-benzyl)-2,5-dimethylpiperazin-1-yl]-2-oxoethoxy}phenyl)-2-(2-iodobenzoylamino)acetamide;

N-(5-chloro-2-{2-[(2RS,5SR)-4-(4-fluoro-$^{18}$F-benzyl)-2,5-dimethylpiperazin-1-yl]-2-oxoethoxy}phenyl)-2-(2-iodobenzoylamino)acetamide;

N-(5-chloro-2-{2-[(2R)-4-(4-fluoro-$^{18}$F-benzyl)-2-methylpiperazin-1-yl]-2-oxoethoxy}phenyl)glycinamide; and N-(5-chloro-2-{2-[(2S)-4-(fluoro-$^{18}$F-benzyl)-2-methylpiperazin-1-yl]-2-oxoethoxy}phenyl)glycinamide;

as well as the mono- and dichloride salts thereof.

The compounds of the present invention may be administered by any suitable route, preferably in the form of a pharmaceutical composition adapted to such a route, and in a dose effective to bind to CCR1 receptors in the brain and thereby be detected by gamma camera or PET. Typically, the administration is parenteral, e.g., intravenously, intraperitoneally, subcutaneously, intradermally, or intramuscularly. Intraveneous administration is preferred.

Thus, for example, the invention provides compositions for parenteral administration which comprise a solution of contrast media dissolved or suspended in an acceptable carrier, e.g., serum or physiological sodium chloride solution.

Aqueous carriers include water, alcoholic/aqueous solutions, saline solutions, parenteral vehicles such as sodium chloride, Ringer□s dextrose, etc. Examples of non-aqueous solvents are propylene glycol, polyethylene glycol, vegetable oil and injectable organic esters such as ethyl oleate.

Other pharmaceutically acceptable carriers, non-toxic excipients, including salts, preservatives, bufers and the like, are described, for instance, in REMMINGTON□S PHARMACEUTICAL SCIENCES, 15$^{th}$ Ed. Easton: Mack Publishing Co., pp. 1405–1412 and 1461–1487 (1975) and THE NATIONAL FORMULARY XIV., 14$^{th}$ Ed. Washington: American Pharmaceutical Association (1975). Aqueous carriers, are preferred.

Pharmaceutical composition of this invention are produced in a manner known per se by suspending or dissolving the compounds of this invention—optionally combined with the additives customary in galenic pharmacy—in an aqueous medium and then optionally sterilizing the suspension or solution. Suitable additives are, for example, physiologically acceptable buffers (such as, for instance, tromethamine), additions of complexing agents (e.g., diethylenetriaminepentaacetic acid) or—if required—electrolytes, e.g., sodium chloride or—if necessary—antioxidants, such as ascorbic acid, for example.

If suspensions or solutions of the compounds of this invention in water or physiological saline solution are desirable for enteral administration or other purposes, they are mixed with one or several of the auxiliary agents (e.g., methylcellulose, lactose, mannitol) and/or tensides (e.g., lecithins, □Tween□, □Myrj□) and/or flavoring agents to improve taste (e.g., ethereal oils), as customary in galenic pharmacy.

The compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For the compounds according to the invention having radioactive halogens, these compounds can be shipped as "hot" compounds, i.e., with the radioactive halogen in the compound and administered in e.g., a physiologically acceptable saline solution. In the case of the metal complexes, these compounds can be shipped as "cold" compounds, i.e., without the radioactive ion, and then mixed with Tc-generator eluate or Re-generator eluate.

Preparation of the Compounds of the Invention

A. Preparation of Compounds of Formula (I)

In general, the radioactive imaging agents of formula (I) of the present invention are prepared by reacting radioactive 4-halobenzyl derivatives with piperazine derivatives. Preferred are $^{18}$F-labeled 4-fluorobenzyl derivatives for PET-imaging. A general method for the preparation of 4-fluoro-$^{18}$F-benzyl halides is described in Iwata et al., *Applied Radiation and Isotopes* (2000), Vol. 52, pp. 87–92.

The $^{18}$F-labeled 4-fluorobenzyl derivatives are prepared by reaction of a benzaldehyde compound of formula (a) with $^{18}$F$^-$ ions to obtain a benzaldehyde compound of formula (b):

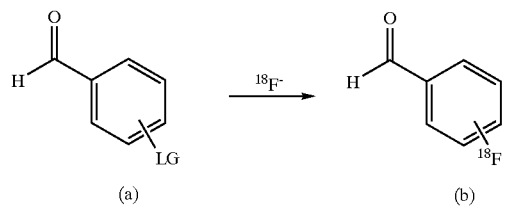

wherein LG is a leaving group, for example, bromo, chloro, iodo, nitro, or N(R)$_3$$^+$X$^-$ (where R is alkyl and X is a halo ion, such as Br$^-$, Cl$^-$, or I$^-$; an ion of a alkanoic acid, such as an acetate ion (CH$_3$C(O)O$^-$); or an ion of an alkylsulfonic acid or haloalkylsulfonic acid, such as triflat (CF$_3$SO$_3$$^-$)). Preferably LG is triflat. Starting from the compound of formula (b), several synthetic pathways are possible in preparing the compounds of formula (I).

In a first synthetic pathway, a compound of formula (b) is reduced with NaBH$_4$ to obtain a compound of formula (c):

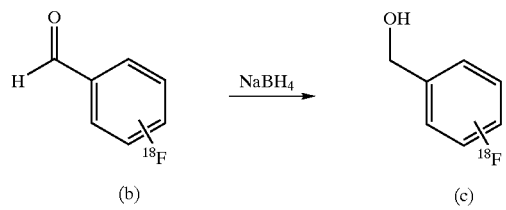

The compound of formula (c) is then reacted with HI, P$_2$I$_4$ or Ph$_3$PBr$_2$ to obtain an iodo- or bromo-substituted compound of formulae (d) or (e):

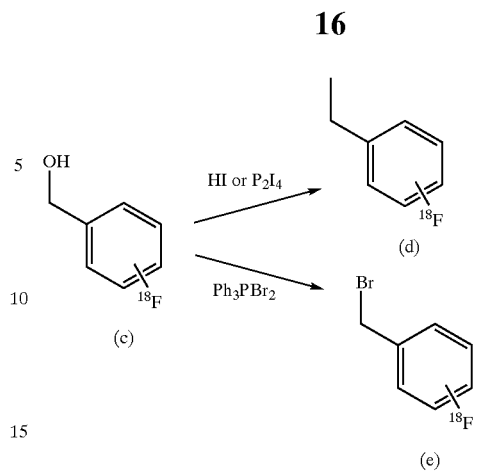

The compounds of formulae (d) and (e) can be obtained with a radiochemical yield of 50 to 60%. The radiochemical purity is greater than 95%. The specific activity of the compounds is 5 mCi per 1 nmol.

A compound of formulae (d) or (e) can then be reacted with a piperazine derivative (f) to obtain a compound of formula (g) (a compound of formula (I)):

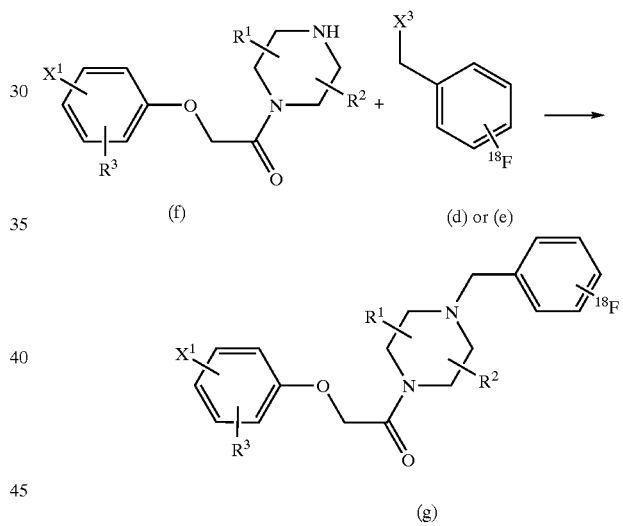

Compounds of formula (f) may be prepared according to methods known to those of ordinary skill in the art and is described in detail in PCT Published Patent Application, WO 98/56771.

In a second synthetic pathway, a compound of formula (b) is directly reacted with a compound of formula (f) using a reducing agent, for example, formic acid, ammonium formiate, NaBH$_4$, or NaBH$_3$CN, to obtain a compound of formula (g) (a compound of formula (I)):

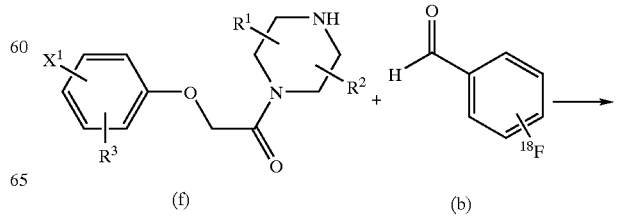

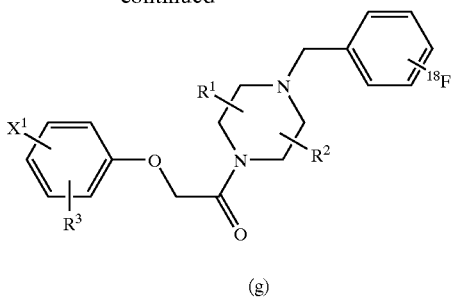

(g)

B. Preparation of Compounds of Formula (II)

For Single Photon Emission Computed Tomography ("SPECT"), $^{99m}$Tc-labeled compounds are preferred. Those compounds are compounds of formula (II). A general synthetic pathway for these compounds starts with non-radioactive analogues of compounds of formula (II) that are reacted with $^{99m}$Tc-binding chelators, e.g. $N_2S2$-Chelators. Preparation of the non-radioactive analogs of the compounds of formula (II) is described in detail in PCT Published Patent Application, WO 98/56771. The synthesis of the chelators follows standard procedures, for example, the procedures described in A. Mahmood et al., *A $N_2S_2$-Tetradentate Chelate for Solid-Phase Synthesis: Technetium, Rhenium in Chemistry and Nuclear Medicine* (1999), Vol. 5, p. 71, or in Z. P. Zhuang et al., *Bioconjugate Chemistry* (1999), Vol. 10, p. 159.

Preferred chelators are chelators of formulae (III) or (IV):

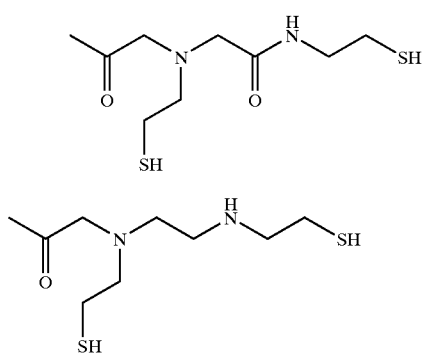

One of the chelators is either bound directly to the nitrogen in the —N($R^4$)$R^5$ group of the non-radioactive compound of formula (II), or via a linker moiety comprising an alkyl radical having one to ten carbon atoms, wherein the alkyl radical optionally contains one to ten —C(O)-groups, one to ten —C(O)N(R)-groups, one to ten —N(R)C(O)- groups, one to ten —N(R)-groups, one to ten —N(R)$_2$ groups, one to ten hydroxy groups, one to ten —C(O)OR— groups, one to ten oxygen atoms, one to ten sulfur atoms, one to ten nitrogen atoms, one to ten halogen atoms, one to ten aryl groups, and one to ten saturated or unsaturated heterocyclic rings wherein R is hydrogen or alkyl. A preferred linker moiety is —C(O)CH$_2$—$_{N(H)}$—.

Without further elaboration, it is believed that one skilled in the art can, using the preceding description, utilize the present invention to its fullest extent. The following specific examples are provided as a guide to assist in the practice of the invention, and are not intended as a limitation on the scope of the invention.

In the foregoing and in the following examples, all temperatures are set forth uncorrected in degrees Celsius and, all parts and percentages are by weight, unless otherwise indicated.

The entire disclosures of all applications, patents and publications, cited above and below, and of corresponding U.S. Provisional Application Ser. No. 60/246,299, filed Nov. 6, 2000, are hereby incorporated by reference.

EXAMPLE 1

Preparation of 1-(5-Chloro-2-{2-[(2R)-2-methylpiprazin-1-yl]-2-oxoethoxy}phenyl)urea

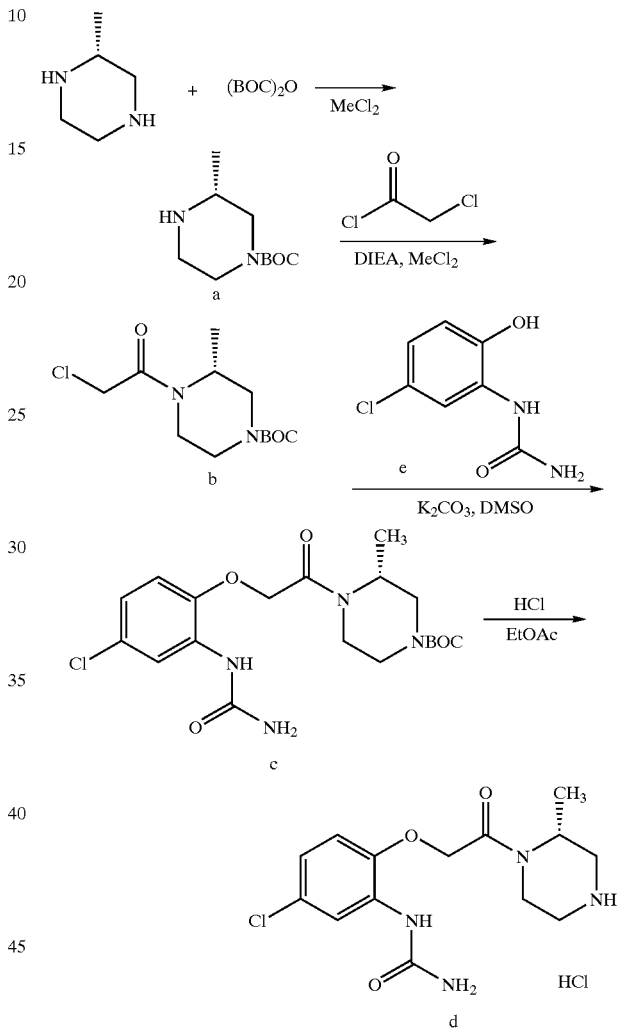

A. DIEA (19.10 mL, 110 mmol) was added to a solution of (R)-(−)-2-methylpiperazine (10 g, 100 mmol) in 250 mL of methylene chloride. The solution was cooled to −10° C. The BOC anhydride was dissolved in 250 mL of methylene chloride and this solution was added to the chilled piperazine solution over 1 hour. The reaction was allowed to warm to ambient temperature over 16 hours. The reaction mixture was filtered to remove the solids and the filtrate washed with 500 mL of water, dried over magnesium sulfate, filtered and evaporated to an oil. The oil was purified by flash column chromatography to afford 11.0 g of the compound of formula (a).

B. The compound of formula (a) (11.0 g, 55 mmol) and DIEA (10.5 mL, 60.4 mmol) were dissolved in 100 mL of methylene chloride. The resulting solution was chilled to −10° C. Chloroacetyl chloride (4.37 mL, 55 mmol) was added dropwise to the solution maintaining the temperature at −10° C. After stirring for 1 hour the reaction mixture was washed with 100 mL of water, dried over magnesium sulfate, filtered and evaporated to an oil. The oil was purified by flash column chromatography to afford 14.8 g of the compound of formula (b).

C. To a solution of the compound of formula (b) (14.8 g, 53.5 mmol) and the compound of formula (e) (9.98 g, 53.5 mmol) in 75 mL of DMSO was added potassium carbonate (18.48 g, 133.7 mmol). The resulting mixture was heated to 50° C. for 3 hours. The mixture was cooled to 30° C. and poured into 700 mL of water. The water was extracted three times with 200 mL of ethyl acetate. The ethyl acetate extracts were combined and washed with 200 mL of 1 N KOH followed by brine. The organic layer was the dried over magnesium sulfate, filtered and evaporated to a foam. The foam was purified by flash column chromatography to afford 19.6 g of the compound of formula (c).

D. The compound of formula (c) (7.68 g, 18 mmol) was dissolved in 40 mL of ethyl acetate. The resulting solution was chilled in an ice bath and anhydrous HCl gas was bubbled through the solution for 5 minutes. The product precipitated while the mixture was allowed to sit at ambient temperature for 1 hour. The product was collected by filtration, washed on the filter with fresh ethyl acetate, and dried under vacuum at ambient temperature to constant weight to afford 5.9 g of 1-(5-chloro-2-{2-[(2R)-2-methylpiperazin-1-yl]-2-oxoethoxy}phenyl)urea, the compound of formula (d), as white solid; NMR (2 rotomers); (400 MHz, DMSO) 9.7 (m, 0.5H), 9.2 (m, 0.5H), 8.16 (s, 1H), 8.13 (s, 0.5H), 6.8 (s, 2H), 4.9 (m, 2H), 4.4 (m, 5H), 3.8 (bs, 0.5H), 3.4, (bs, 0.5H), 3.2, (m, 2.5H), 3.0 (m, 2 H) 1.2–1.4 (m, 3H) ppm.

EXAMPLE 2

Preparation of the Compound of Formula (e)

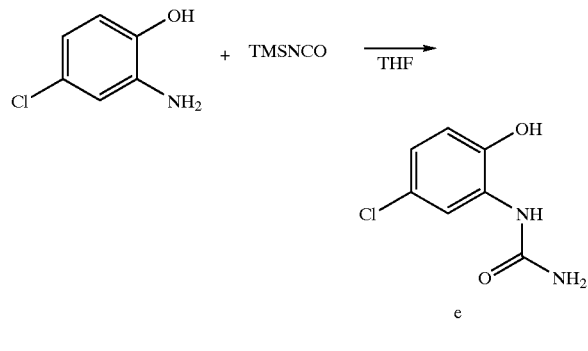

To a solution of 2-amino-4-chlorophenol (10 g, 69.7 mmol) in 100 mL of anhydrous THF at ambient temperature was added trimethylsilyl isocyanate (18.8 mL, 139.4 mmol) in one portion. The solution was heated to 60° C. and remained at this temperature for 22 hours at which time water (1.3 mL, 76.7 mmol) was added. After 30 minutes the solution was cooled to ambient temperature and concentrated to a brown oil. This oil was dissolved in ethyl acetate, treated with activated carbon, dried over magnesium sulfate and filtered. The filtrate was concentrated to a pink solid which was crystallized from 10:1, toluene/methanol to give 5.4 g of the compound of formula (e) as tan powder.

EXAMPLE 3

Preparation of 1-(5-Chloro-2-{2-[(2R)-4-(4-fluoro-$^{18}$F-benzyl)-2-methylpiperazin-1-yl]-2-oxoethoxy}phenyl)urea A. Hydrogen fluoride-$^{18}$F was prepared in a cyclotron by bombardment of $H_2O$—$^{18}O$ with protons. The resulting hydrogen fluoride-$^{18}$F was adsorbed on an anion-exchange cartridge. The hydrogen fluoride-$^{18}$F was eluted with a solution of Kryptofix 222 (15 mg, 40 μmol) and $K_2CO_3$ (2.77 mg, 20 μmol) in aqueous acetonitrile (1.5 mL, 66%). The radioactive fractions were evaporated to dryness in a nitrogen gas stream. This procedure was repeated three times with dry acetonitrile (1 mL). After addition of a solution of 4-trimethylammonium-benzaldehyde-triflate (2 mg, 6.4 μmol) in dry DMF (250 μl) the resulting reaction mixture was heated for 5 minutes to 100° C. After cooling to ambient temperature a solution of 1-(5-chloro-2-{2-((2R)-2-methylpiperazin-1-yl]-2-oxoethoxy}phenyl)urea, a compound of formula (d), (3 mg, 8.3 μmol) in 50 μl acetic acid and a solution of sodium-cyano-borhydride (4 mg, 63.7 μmol) in 100 μl dry DMF were added. The reaction mixture was heated to 120° C. for 10 minutes. After addition of 5 mL of water the mixture was filtered over a polystyrol-cartridge. The adsorbed product was washed with 2 mL of water to afford the title compound, 1-(5-chloro-2-{2-[(2R)-4-(4-fluoro-$^{18}$F-benzyl)-2-methylpiperazin-1-yl]-2-oxoethoxy}phenyl)urea, which was eluted with 1.5 mL acetonitrile and purified by HPLC.

B. In a similar manner, other compounds of formula (I) containing a $^{18}$F atom are prepared.

EXAMPLE 4

Preparation of N-(5-Chloro-2-{2-[(2R)-4-(4-fluorobenzyl)-2-methylpiperazin-1-yl]-2-oxoethoxy}phenyl)glycinamide

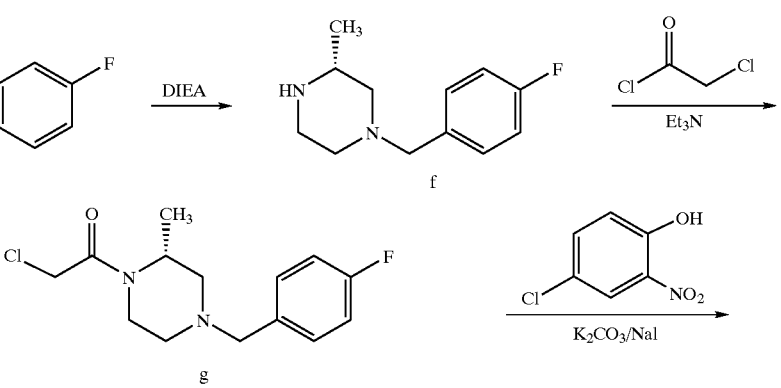

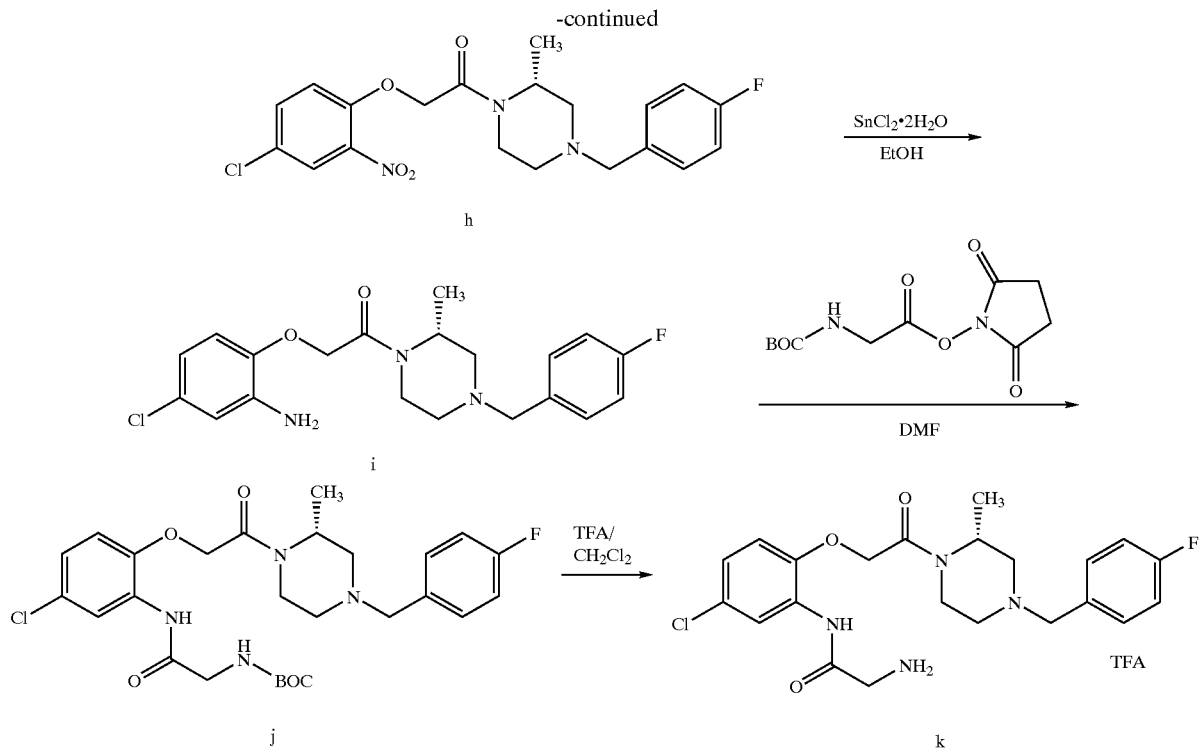

A. To a solution of (R)-(−)-2-methylpiperazine (2.0 g, 20 mmol) in 20 mL CH$_2$Cl$_2$ was added DIEA (5.29, 40 mmol) and 4-fluorobenzyl chloride (2.39 mL 20 mmol). The resulting mixture was stirred at ambient temperature for 15 hours. After the reaction was completed, the reaction mixture was washed with water (3×20 mL) and brine, then dried over Na$_2$SO$_4$, filtered and concentrated in vacuo to afford the compound of formula (f) (2.2 g) as a white solid.

B. To a solution of the compound of formula (f) (2.2 g, 10 mmol) in 50 mL CH$_2$Cl$_2$ was added chloroacetyl chloride (0.84 mL, 10 mmol). The resulting mixture was stirred at ambient temperature for 10 minutes and then triethylamine (3 mL, 21 mmol) was added. After 30 minutes, the mixture was washed with water (3×20 mL) and brine, then dried over Na$_2$SO$_4$, filtered and concentrated in vacuo to afford an oil. Purification by flash column chromatography afforded the compound of formula (g) (2.5 g).

C. To a solution of the compound of formula (g) (2.4 g, 8.4 mmol) in 50 mL DMF was added K$_2$CO$_3$ (2.5 g, 17 mmol), NaI (0.2 g) and 4-chloro-2-nitrophenol (1.3 g, 8.4 mmol). The resulting mixture was heated at 70–80° C. After 1 hour, the mixture was concentrated in vacuo, then taken up in ethyl acetate (150 mL) and washed with water (3×100 mL) and then brine. The organic layer was separated, dried over Na$_2$SO$_4$, filtered and concentrated in vacuo to afford an oil. Purification by flash column chromatography afforded the compound of formula (h) (3.1 g).

D. To a solution of the compound of formula (h) (1.1 g, 2.6 mmol) in 10 mL ethanol was added a solution of tin(II) chloride dihydrate (3.0 g, 13 mmol) in 5 mL ethanol. The resulting mixture was heated at 75° C. After 1 hour, the reaction was concentrated in vacuo, then taken in ethyl acetate (100 mL), washed with 1 N NaOH solution in water (3×100 mL) and brine. The organic layer was separated, dried over Na$_2$SO$_4$, filtered and concentrated in vacuo to afford an oil. Purification by flash column chromatography afforded the compound of formula (i) (0.75 g).

E. To a solution of the compound of formula (i) (0.7 g, 1.78 mmol) in 10 mL DMF was added BOC-Gly-OSU (0.58 g, 2.13 mmol). The resulting mixture was heated at 50–60° C. After 24 hours, the mixture was concentrated in vacuo, then taken up in ethyl acetate (150 mL) and washed with water (3×100 mL) and then brine. The organic layer was separated, dried over Na$_2$SO$_4$, filtered and concentrated in vacuo to afford an oil. Purification by flash column chromatography afforded the compound of formula (j) (0.7 g).

F. To a solution of the compound of formula (j) (0.6 g, 1.1 mmol) in 10 mL CH$_2$Cl$_2$ was added TFA (5 mL). The resulting mixture was heated at ambient temperature. After the reaction was completed in 1 hour, the reaction was concentrated in vacuo, then taken up in ethyl acetate (100 mL), washed with 1N NaOH solution in water (2×100 mL) and brine. The organic layer was separated, dried over Na$_2$SO$_4$, filtered and concentrated in vacuo to afford an oil. Purification by flash column chromatography afforded N-(5-chloro-2-{2-[(2R)-4-(4-fluorobenzyl)-2-methylpiperazin-1-yl]-2-oxoethoxy}phenyl)glycinamide, the compound of formula (k), (0.45 g) as a white solid; NMR (CDCl$_3$) 10.2 (s, 1), 8.5 (s, 1), 7.3 (m, 2), 7.0 (m, 3), 6.8 (d, 1), 4.7 (m, 2), 3.4–3.6 (m, 5), 3.0 (m, 1), 2.8 (m, 1), 2.6 (d, 1), 2.2 (m, 1), 2.0 (m, 2), 1.2–1.4 (m, 3) ppm.

EXAMPLE 5

N'-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide, Technetium-99m-complex A. To a stirred solution of N-{5-chloro-2-[2-[4-(4-fluorobenzyl)-2-(2R)-methylpiperazin-1-yl]-2-oxoethoxy]phen-1-yl}glycinamide (175.5 mg, 0.4 mmol) (the compound of formula (k) as prepared above in Example 4), N—(S-trityl-2-mercaptoeth-1-yl) -N—(S-trityl-5-mercapto- 3-aza-2-oxopent-1-yl)glycine (291.4 mg, 0.4 mmol) (which can be synthesized according to A. Mahmood et al., *A $N_2S_2$-Tetradentate Chelate for Solid-Phase Synthesis: Technetium, Rhenium in Chemistry and Nuclear Medicine* (1999), Vol. 71), and N-hydroxysuccinimide (45.5 mg, 0.4 mmol) in 5 mL dichloromethane was added dropwise a solution of dicyclohexylcarbodiimide (81.4 mg, 0.4 mmol) in 3 mL dichloromethane. The resulting suspension was stirred over night at ambient temperature. After filtration, the resulting solution was evaporated under reduced pressure. The desired product, N'-(S-trityl-2-sulfanyleth-1-yl)-N'-(S-trityl-5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide (340 mg, 72.8%) was isolated after silica gel chromatography (eluent: dichloromethane/methanol, 98:2) as a white powder.

| Elemental Analysis: | | | | |
|---|---|---|---|---|
| Calc.: C 69.93 | H 5.87 | N 7.20 | O 6.85 | S 5.49 |
| Found: C 69.69 | H 6.05 | N 7.01 | O | S 5.32 |

B. N'-(S-Trityl-2-sulfanyleth-1-yl)-N'-(S-trityl-5-mercapto-3-aza-2-oxopent-1-yl)-N -{5-chloro-2-[2-[4-(4-fluorobenzyl)-2-(2R)-methylpiperazin-1-yl]-2-oxoethoxy]phen-1-yl}glycylglycinamide (116.8 mg, 0.1 mmol), as prepared above, was dissolved in 5 mL trifluoroacetic acid. After addition of triethyl silane (48 μl, 0.3 mmol) the resulting suspension was stirred for 15 minutes at ambient temperature. The fitrate was evaporated under reduced pressure and the residue was triturated with 7 mL diethyl ether. The precipitate was stirred for 1 hour at ambient temperature and filtered off, yielding the desired product, N'-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide, bis-trifluoracetic acid salt (87 mg, 95.5%), as a white solid.

| Elemental Analysis: | | | | |
|---|---|---|---|---|
| Calc.: C 44.81 | H 4.65 | N 9.22 | O 15.80 | S 7.04 |
| Found: C 44.54 | H 4.91 | N 8.99 | O | S 6.80 |

C. Disodium tartrate (1 mg) and N'-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide, bis-trifluoracetic acid salt (100 μg), as prepared above, were dissolved in 500 μl sodium phosphate buffer (0.1 M, pH=8.5). After addition of 37MBq $^{99m}$Tc-generator eluate, 5 μl tin-(II) chloride solution was added and the mixture was heated for 10 min to 100° C. HPLC analysis showed a major peak indicating that the desired product, N'-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycylglycinamide, Technetium-99m-complex, was synthesized with a RCP>90%.

EXAMPLE 6

Preparation of 1-(2-{2-[(2R)-4-(4-Fluorobenzyl)-2-methylpiperazin-1-yl]-2-oxoethoxy}-5-iodophenyl) urea

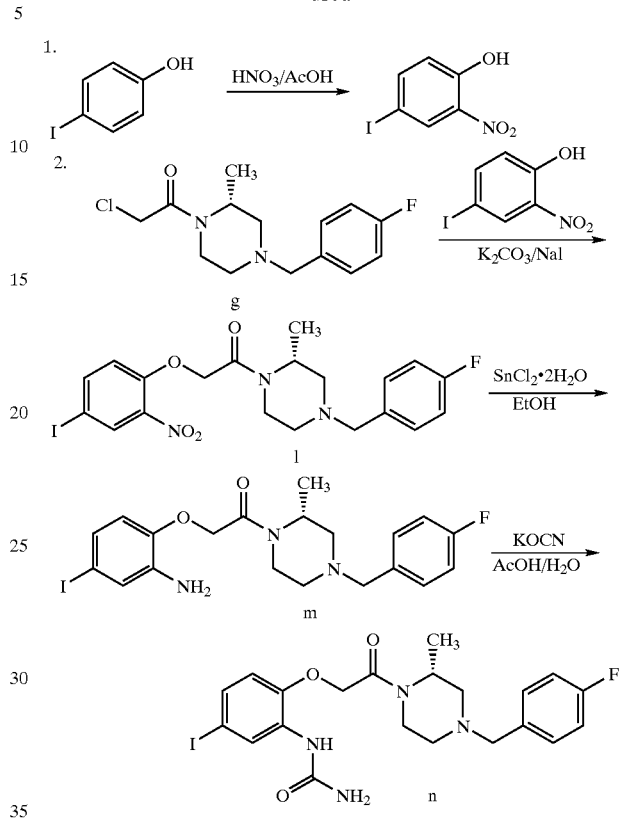

A. To a solution of p-iodophenol (2.2 g, 10 mmol) in 18 mL acetic acid was added a solution of $HNO_3$ (0.7 mL, 70%) in 5 mL acetic acid dropwise over 10 minutes. The resulting mixture was stirred at ambient temperature. After 30 minutes, the reaction mixture was diluted by 100 mL ice-water. The precipitate was collected, washed with 100 mL water. Purification by flash column chromatography afforded 1.2 g of 2-nitro-4-iodophenol.

B. To a solution of the compound of formula (g) (0.3 g, 1.05 mmol) (as prepared herein) in 10 mL DMF was added $K_2CO_3$ (0.45 g, 3.2 mmol), NaI (0.01 g) and 2-nitro-4-iodophenol (0.28 g, 1.05 mmol). The resulting mixture was heated at 70–80° C. After 1 hour, the mixture was concentrated in vacuo, then taken up in ethyl acetate (150 mL) and washed with water (3×100 mL)and then brine. The organic layer was separated, dried over $Na_2SO_4$, filtered and concentrated in vacuo to afford an oil. Purification by flash column chromatography afforded 0.28 of the compound of formula (l).

C. To a solution of the compound of formula (l) (0.28 g, 0.55 mmol) in 5 mL ethanol was added a solution of Tin(II) chloride dehydrate (0.616 g, 2.73 mmol) in 5 mL ethanol. The resulting mixture was heated at 75° C. After 1 hour, the reaction was concentrated in vacuo, then taken up in ethyl acetate (100 mL), washed with 1N NaOH solution in water (3×100 mL) and brine. The organic layer was separated, dried over $Na_2SO_4$, filtered and concentrated in vacuo to afford an oil. Purification by flash column chromatography afforded the compound of formula (m) (0.25 g).

D. To a solution of the compound of formula (m) (0.25 g, 0.52 mmol) in 3 mL AcOH was added water (6 mL). The resulting mixture was stirred at ambient temperature for 10 minutes, then a solution of KOCN (0.085 g, 1.0 mmol) in 1 mL water was added dropwise. The reaction mixture was stirred at ambient temperature for 10 minutes, then heated at 55° C. for 5 minutes. After the reaction was completed, the reaction mixture was concentrated in vacuo, then taken up in $CH_2Cl_2$ (50 mL), washed with 2N NaOH solution in water (2×100 mL) and brine. The organic layer was separated, dried over $Na_2SO_4$, filtered and concentrated in vacuo to afford an oil. Purification by flash column chromatography afforded the compound of formula (n) (0.16 g) as a white solid; NMR ($CDCl_3$) 9.0 (s, 1), 8.6 (s, 1), 7.3 (m, 2), 7.0 (t, 3), 6.6 (d, 1), 4.9 (s, 2), 4.7 (m, 2), 4.4 (m, 1), 3.4–3.6 (m, 3), 3.0 (m, 1) 2.8 (m, 1), 2.6 (d, 1), 2.2 (m, 1), 2.0 (m, 1), 1.2–1.4 (m, 3) ppm.

EXAMPLE 7

Preparation of 1-(2-{2-[(2R)-4-(4-Fluorobenzyl)-2-methylpiperazin-1-y]-2-oxoethoxy}-5-iodo-$^{123}$I-phenyl)urea A. To a solution of the compound of formula (n) (1 mg), as prepared above, and 10 μg copper-(II)-sulfate in 300 μl DMF was added 1 mCi sodium iodine[$^{123}$I] solution. The resulting reaction mixture was heated over night to 100° C. After adding of 1 mL half-saturated aqueous $NaHCO_3$ solution the product was extracted with 2 mL $CH_2Cl_2$. The organic layer was evaporated to dryness in a nitrogen gas stream. The desired product, 1-(2-{2-[(2R)-4-(4-fluorobenzyl)-2-methylpiperazin-1-yl]-2-oxoethoxy}-5-iodo-$^{123}$I-phenyl)urea, was purified using a RP-cartridge [eluant: EtOH/water (2:1)].

B. In a similar manner as described above, other compounds of formula (I) are prepared.

EXAMPLE 8

N'-(2-Mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycinamide, Technetium-99m-complex A. To a stirred solution of 156.7 mg (0.4 mmol) 5-chloro-2-[2-[4-(4-fluorobenzyl)-2-(2R)-methylpiperazin-1-yl]-2-oxoethoxy]aniline (compound of formula (i)) (291.4 mg, 0.4 mmol), N—(S-trityl-2-mercaptoeth-1-yl)-N—(S-trityl-5-mercapto-3-aza-2-oxopent-1-yl)glycine (synthesized according to A. Mahmood et at., *A $N_2S_2$-Tetradentate Chelate for Solid-Phase Synthesis: Technetium, Rhenium in Chemistry and Nuclear Medicine* (1999), Vol. 5, p. 71) and N-hydroxysuccinimide (45.5 mg, 0.4 mmol) in 5 mL dichloromethane was added dropwise a solution of dicyclohexylcarbodiimide (81.4 mg, 0.4 mmol) in 3 mL dichloromethane. The resulting suspension was stirred over night at ambient temperature. After filtration, the resulting solution was evaporated under reduced pressure. The desired product, N'-(S-trityl-2-mercaptoeth-1-yl)-N'—(S-trityl-5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycinamide (352 mg, 79.2%), was isolated after silica gel chromatography (eluent: dichloromethane/methanol, 98:2) as a white powder.

| Elemental Analysis: | | | | | |
|---|---|---|---|---|---|
| Calc.: | C 71.36 | H 5.90 | N 6.30 | O 5.76 | S 5.77 |
| Found: | C 71.08 | H 6.13 | N 6.05 | O | S 5.52 |

B. N'-(S-trityl-2-mercaptoeth-1-yl)-N'-(S-trityl-5-mercapto-3-aza-2-oxopent-1-yl)-N -{5-chloro-2-[2-[4-(4-fluorobenzyl)-2-(2R)-methylpiperazin-1-yl]-2-oxoethoxy]-phen-1-yl}glycinamide (111.1 mg, 0.1 mmol) was dissolved in 5 mL trifluoroacetic acid. After addition of 48 pl (0.3 mmol) triethyl silane the resulting suspension was stirred for 15 min at ambient temperature. The fitrate was evaporated under reduced pressure and the residue was triturated with 7 mL diethyl ether. The precipitate was stirred for 1 hour at ambient temperature and filtered off, yielding the desired product, N-(2-mercaptoeth-1-yl)-N'-(5-mercapto-3-aza-2-oxopent-1-yl)-N-{5-chloro-2-[2-[4(4-fluorobenzyl)-2-(2R)-methylpiperazin-1-yl]-2-oxoethoxy]phen-1-yl}glycinamide, bis-trifluoracetic acid salt (75 mg, 87.8%) as a white solid.

| Elemental Analysis: | | | | | |
|---|---|---|---|---|---|
| Calc.: | C 44.99 | H 4.60 | N 8.20 | O 14.98 | S 7.51 |
| Found: | C 44.71 | H 4.89 | N 8.03 | O | S 7.22 |

C. Disodium tartrate (1 mg) disodium tartrate and N'-(2-mercaptoeth-1-yl)-N'-(5-mercapto-3-aza-2-oxopent-1-yl)-N-{5-chloro-2-[2-4-(4-fluorobenzyl)-2-(2R)-methylpiperazin-1-yl]-2-oxoethoxy]phen-1-yl}glycinamide, bis-trifluoracetic acid salt (100 μg) were dissolved in 500 μl sodium phosphate buffer (0.1M, pH=8.5). After addition of 37.5 MBq $^{99m}$Tc-generator eluate, 5 μl tin-(II) chloride solution was added and the mixture was heated for 10 minutes to 100° C. HPLC-analysis showed a major peak indicating that the desired product, N'-(2-mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycinamide, technetium-99m-complex was synthesized with a RCP>91%.

EXAMPLE 9

N'-(2-Mercaptoeth-1-yl)-N'-(5-mercapto-3 azapent-1-yl)-N-{5-chloro-2-[2-[4-(4-fluorobenzyl)-2-(2R)-methylpiperazin-1-yl]-2-oxoethoxy]phen-1-yl}glycinamide, Technetium-99m-complex A. To a stirred solution of 5-chloro-2-[2-[4-(4-fluorobenzyl)-2-(2R)-methylpiperazin-1-yl]-2-oxoethoxy]aniline (156.7 mg, 0.4 mmol) and triethylamine (40.5 mg, 0.4 mmol) in 5 mL dichloromethane was added dropwise a solution of α-bromoacetyl chloride (63 mg, 0.4 mmol) in 3 mL dichloromethane. The resulting solution was stirred over night at ambient temperature. The solvent was evaporated under reduced pressure. The desired product, N-{5-chloro-2-[2-[4-(4-fluorobenzyl)-2-(2R)-methylpiperazin-1-yl]-2-oxoethoxy]phen-1-yl}2bromoacetamide (175 mg, 85.3%), was isolated after silica gel chromatography (eluent: dichloromethane/methanol, 99:1) as a white powder.

| Elemental Analysis: | | | | |
|---|---|---|---|---|
| Calc.: | C 51.53 | H 4.72 | N 8.19 | O 5.76 |
| Found: | C 51.28 | H 4.99 | N 7.92 | O |

B. A stirred solution of N-{5-chloro-2-[2-[4-(4-fluorobenzyl)-2-(2R)-methylpiperazin-1-yl]-2-oxoethoxy]phen-1-yl}-2-bromoacetamide (165 mg, 0.42 mmol) and N,N'-bis-(S-(4-methoxybenzyl)-2-mercaptoeth-1-yl)ethylenediamine (841.3 mg, 2 mmol) (synthesized according to Z. P. Zhuang et al., *Bioconjugate Chem.* (1999), Vol. 10, p. 159) in 1,4-dioxane (5 mL) was heated under reflux for 24 hours. The resulting reaction mixture was evaporated under reduced pressure. The residue was dissolved in 15 mL dichloromethane and washed with saturated aqueous sodium carbonate solution. After drying over $MgSO_4$ the solvent was evaporated under reduced pressure. The desired product, N'-(S-(4-methoxybenzyl)-2-mercaptoeth-1-yl)-N'-(S-(4'-methoxybenzyl)-5-mercapto-3-azapent-1-yl)-N-{5-chloro-2-[2-[4-(4-(4-fluorobenzyl)-2-(2R)methylpiperazin-1-yl]-2-oxoethoxy]phen-1-yl}glycinamide (154 mg, 43%), was isolated after silica gel chromatography (eluent: dichloromethane/methanol, 9:1) as a white powder.

| Elemental Analysis: | | | | | |
|---|---|---|---|---|---|
| Calc. | C 61.99 | H 6.50 | N 8.22 | O 9.38 | S 7.52 |
| Found: | C 61.71 | H 6.58 | N 8.03 | O | S 7.28 |

C. N'-(S-(4-methoxybenzyl)-2-mercaptoeth-1-yl)-N'-(S-(4'-methoxybenzyl)-5-mercapto-3-azapent-1-yl)-N-{5-chloro-2-[2-[4-(4-fluorobenzyl)-2-(2R)-methylpiperazin-1-yl]-2-oxoethoxy]phen-1-yl}glycinamide (140 mg, 0.164 mmol) was dissolved at 0° C. in 5 mL trifluoroacetic acid. After addition of $Hg(OAc)_2$ (104.5 mg, 0.328 mmol) the resulting mixture was stirred for 30 minutes at 0° C. and saturated for 15 min with $H_2S$. After filtration the solvent was evaporated under reduced pressure. The resulting yellow oil was triturated with 3 mL diethyl ether. The desired product, N'-(2-mercaptoeth-1-yl)-N'-(5-mercapto-3-azapent-1-yl)-N-{5-chloro-2-(2-[2-[4-(4-fluorobenzyl)-2-(2R)-methylpiperazin-1-yl]-2-oxoethoxy]phen-1-yl}glycinamide, tris-trifluoracetic acid salt (126 mg (80.5%), was isolated after filtration as a white powder.

| Elemental Analysis: | | | | | |
|---|---|---|---|---|---|
| Calc.: | C 42.79 | H 4.44 | N 7.34 | O 15.09 | S 6.72 |
| Found: | C 42.48 | H 4.73 | N 7.02 | O | S 6.76 |

D. Disodium tartrate (1 mg) and N'-(2-mercaptoeth-1-yl)-N'-(5-mercapto-3-azapent-1-yl)-N-{5-chloro-2-[2-[4-(4-fluorobenzyl)-2-(2R)-methylpiperazin-1-yl]-2-oxoethoxy]phen-1-yl}glycinamide, tris-trifluoracetic acid salt (100 μg) were dissolved in 500 μl sodium phosphate buffer (0.1M, pH=8.5). After addition of 37.5 MBq $^{99m}$Tc-generator eluate, 5 μl tin-(II) chloride solution was added and the mixture was heated for 10 minutes to 100° C. HPLC-analysis showed a major peak indicating that the desired product, N'-(2-mercaptoeth-1-yl)-N'-(5-mercapto-3-azapent-1-yl)-N-{5-chloro-2-[2-[4-(4-fluorobenzyl)-2-(2R)-methylpiperazin-1-yl]-2-oxoethoxy]phen-1-yl}glycinamide. Technetium-99m-complex, was synthesized with a RCP>95%.

EXAMPLE 10

Immunohistochemical Localization of CCR1 in Human Brains

Materials and Methods

A first group of tissue samples from brains that had been obtained at autopsy within 12 hours of death was used for immunohistochemical staining of the chemokine receptor CCR1 in Alzheimer's disease and control brains. Paraffin-embedded, 5-μm-thick, unstained sections from frontal cortex and hippocampus were used for all immunohistochemical and histochemical stains.

Slides were de-paraffinized in xylene and hydrated to phosphate-buffered saline containing 0.005% Triton X100 (PBS-T). For light microscopy (using DAB as chromogen) endogenous peroxidase activity was blocked by incubating the slides with 0.01% $H_2O_2$ in methanol for 30 minutes. Non-specific binding was reduced by blocking in 10% normal goat serum (NGS) in PBS for 30 minutes. The primary antibodies [Rabbit anti-CCR1, (N-terminal peptide); Mouse anti-Neurofilament; mouse anti-GFAP; mouse anti-Tau (AT8); mouse anti-CD68 (clone KP1); mouse anti-β-amyloid (Boehringer Mannheim, #1 381 431); Rabbit anti-CCR8, (N-terminal peptide)] were diluted in PBS-T and slides were incubated overnight at room temperature. Staining was completed using a Biogenex ABC™ kit. All washes used PBS-T. After the DAB reaction was completed, slides were lightly counterstained with Gill's Hematoxylin, dehydrated and coverslipped with Permount. Before coverslipping, some slides were re-stained with antibodies against Aβ peptide using identical methods except that the chromogen was True Blue™. For immunofluorescent double-labeling studies the slides were de-paraffinized, blocked with 10% NGS, and incubated with a cocktail of both primary antibodies overnight. The slides were washed with PBS-T and then incubated with a cocktail of goat secondary antibodies, each at 1/50 dilution. To avoid confusion from endogenous (yellow-green) tissue fluorescence, the secondary antibodies were conjugated to either Cy3 ($\epsilon_{max}$=565 nm; goat-anti-mouse, Amersham) or Cy5 ($\epsilon_{max}$=700 nm; goat-anti-rabbit, Amersham). Slides were viewed on a confocal microscope with a krypton-argon laser (model 2010, Molecular Dynamics, Sunnyvale, Calif.).

Subsequently, a second group of brain tissues composed of 10 cases from cognitively normal elderly and 40 cases from Alzheimer's disease patients who had been assessed for clinical dementia rating (CDR) were obtained and evaluated for immunohistochemical expression of CCR1. The samples were stained for CCR1 and other markers as described above except that monoclonal antibodies (clone #6D5) specific for $A\beta^{1-42}$ (a marker for diffuse, early amyloid deposits as well as for more mature neuritic plaques) were obtained from Dr. Ursula Moenning. These antibodies were visualized with Vector Red™ (Vector Labs). Dr Moenning also provided monoclonal antibodies specific for $A\beta^{1-40}$ (clone #13E9), a marker for plaques found in late-stage disease, that was visualized with True Blue™.

Results

In both sets of brains, areas with Alzheimer's disease pathology showed a characteristic staining pattern. CCR1 immunoreactivity was found in association with neuritic (i.e., senile) plaques in both the hippocampal formation and the cerebral cortex. The immunostained structures were round to ovoid and were not usually associated with cell bodies. They varied in size and appeared to be filled with a punctate granular material. These structures were found to form "coronas" around the amyloid deposits in senile plaques, but were distinct from the Aβ itself (FIGS. 14). The top panel in FIG. 1 shows a neuritic plaque with a corona of CCR1-positive processes. Neuronal cell bodies of some CA1 and CA3 neurons in Alzheimer's disease cases were sometimes stained by CCR1 antibodies. The bottom panel in FIG. 1 illustrates this finding. This staining was distinct from neurofibrillary tangles (NFT) or granulovacuolar bodies, although it was commonly present in the somata of neurons with these degenerative changes.

Figure 2:
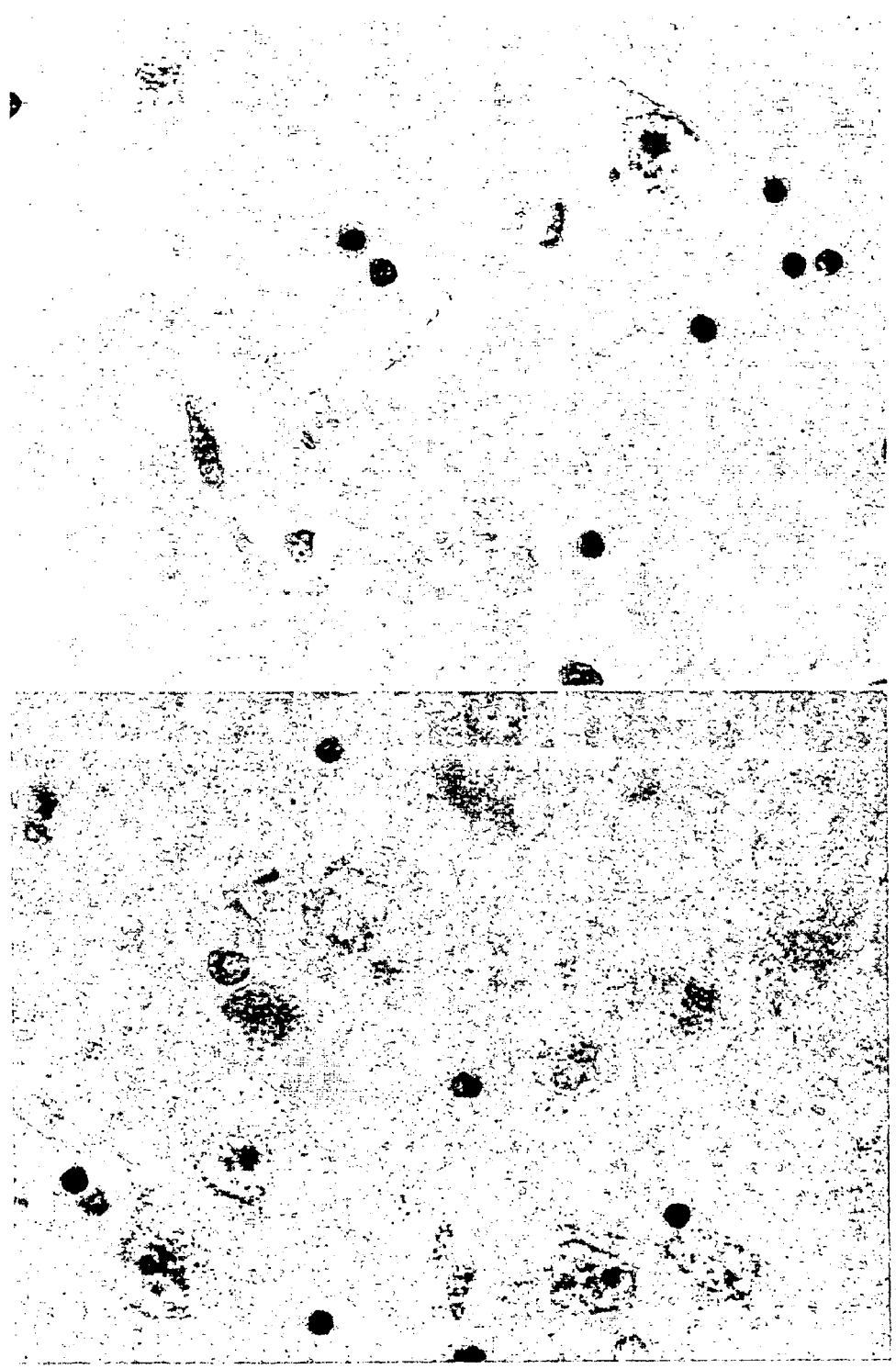
FIG. 2 shows CCR1 antibody specificity in Alzheimer's disease brain tissue.

Pre-incubation of antibodies with a 16-mer polypeptide from the extracellular (N-terminus) region of the CCR1 receptor protein completely blocked all tissue staining, as illustrated in FIG. 2. In particular, the top image in FIG. 2 shows a lack of staining in Alzheimer's disease brain with CCR1 antibodies that were pre-incubated with the polypeptide while the bottom image in FIG. 2 shows many CCR 1-positive structures in a sister section stained with un-incubated antibodies.

Figure 3:
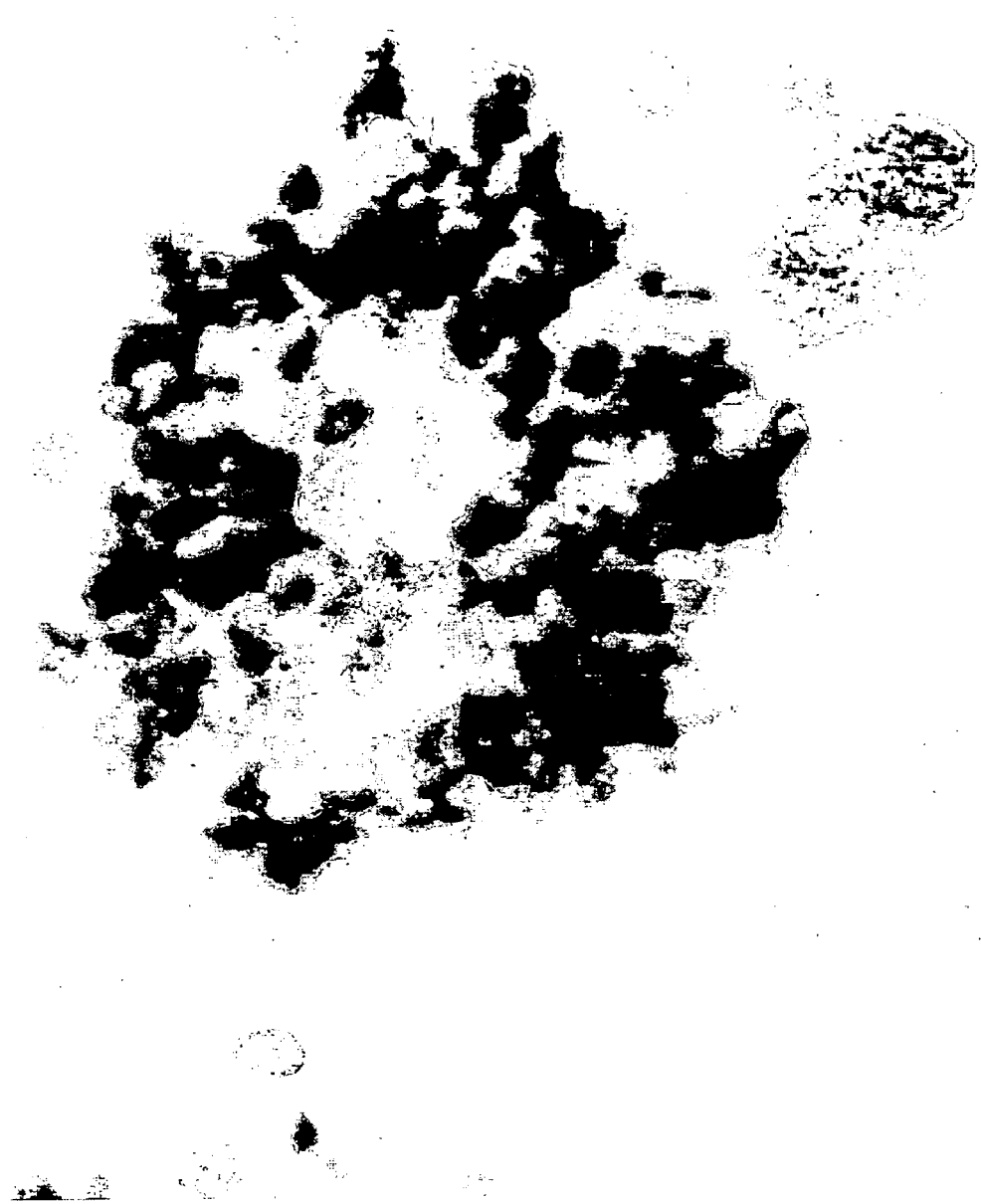
FIG. 3 shows CCR1-$A\beta^{1-40}$ double-labeled tissue sections
Figure 4:
FIG. 4 shows neuritic plaques double-labeled for CCR1 and $A\beta^{1-42}$.

Double-labeling studies showed that nearly all CCR1-positive structures were associated with neuritic plaques containing $A\beta^{1-42}$ as shown in FIG. 4. $A\beta^{1-42}$ in diffuse plaques (FIG. 5) was not typically associated with CCR1 nor with any significant cellular responses. In more advanced cases of Alzheimer's disease, many more $A\beta^{1-40}$-positive plaques were seen. Some, but not all of these were associated with CCR1 staining as shown in FIG. 3. In some cases CCR1-positive plaques were completely free of $A\beta^{1-40}$ staining.

In cases of severe Alzheimer's disease where significant neuronal loss and gliosis were seen, reactive astrocytes in the subiculum and entorhinal cortex were also CCR1 positive. In less severe cases, CCR1-positive reactive astrocytes were uncommon.

Confocal microscopy of double-labeled sections showed that CCR1 immunoreactivity co-localized with neurofilament-positive processes. The macrophage/microglial marker, CD68, was not associated with CCR1 staining, nor was the AT8 antibody against abnormally phosphorylated tau protein. As expected from light microscopic studies, CCR1 immunoreactivity did co-localize with GFAP in areas of astrogliosis.

Figure 5:
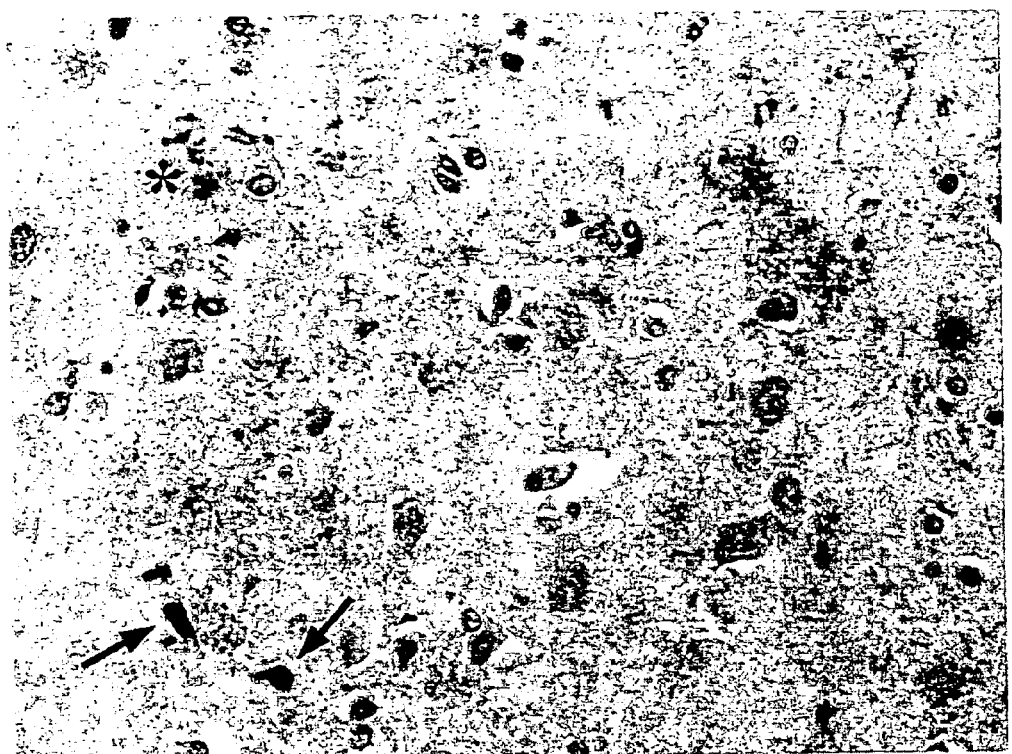
FIG. 5 shows diffuse $A\beta^{1-42}$ staining in Alzheimer's disease brain.

Leukocytes present within cerebral vessels were strongly CCR1 positive in both Alzheimer's disease and control brain tissues, serving as positive internal controls for staining methods. In FIG. 5 note the CCR1-positive staining of two intravascular cells (arrows). Some CCR1-positive material is also seen at asterisk, but in general, diffuse plaques are not associated with CCR1.

Using hippocampal tissue from the second study (where patients were grouped into known clinical categories by CDR score), a quantitative evaluation of the number of CCR1-positive plaque-like structures in the hippocampus was undertaken. Histologic evaluations of individual sections were performed under blinded conditions with respect to clinical (CDR) status. The volume analyses were conducted using unbiased computerized methods.

Figure 6:
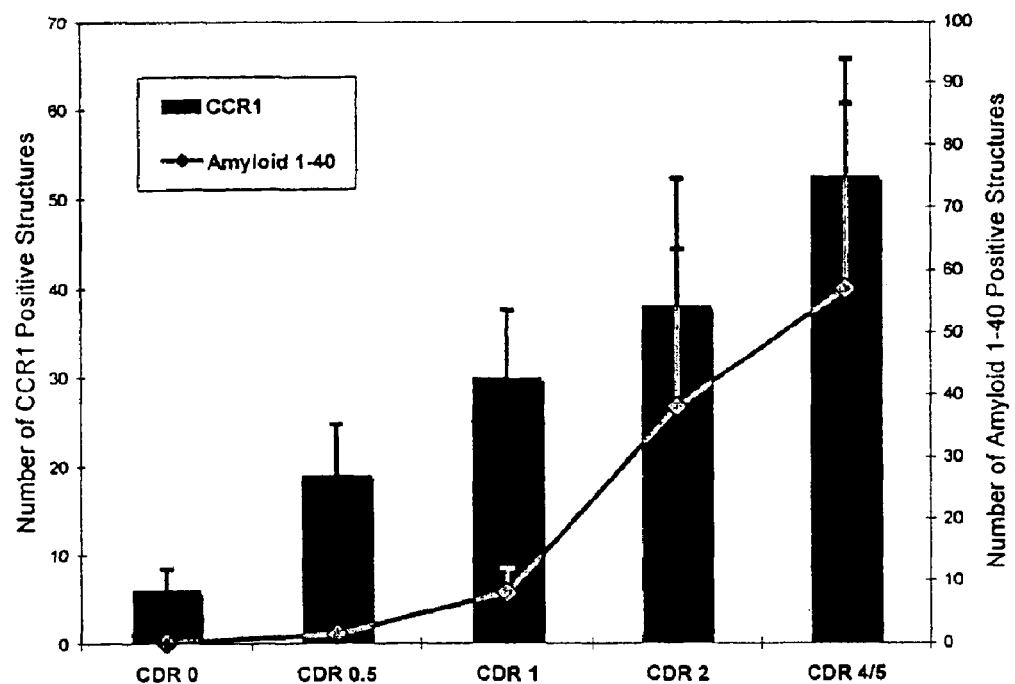
FIG. 6 is a graph showing the relationship between CCR1 and $A\beta^{1-40}$ by CDR score.

FIG. 3 demonstrates the histologic relationship between CCR1-positive dystrophic neurites (brown stain) and a neuritic plaque containing $A\beta^{1-40}$ (blue stain). Note in that in FIG. 3 the CCR1-positive processes are distinct from the amyloid. Plaques containing $A\beta^{1-40}$ were discrete and easily counted, as were the clusters of CCR1-positive neurites. Slides of hippocampus were evaluated for the number of CCR1-positive coronas, the number of $A\beta^{1-40}$ positive plaques, and the number of plaques containing both markers. The structures were counted by region (e.g., CA3, CA1, and subiculum) within the entire hippocampal formation, including entorhinal cortex and then totaled. The values are relative estimates of the number of structures in the hippocampus as represented by 5-$\mu$m thick cross-sections of the hippocampal formation. FIG. 6 shows the relationship between CCR1 and $A\beta^{1-40}$ by CDR score.

Quantification of the amount of $A\beta^{1-42}$ required a different technique because $A\beta^{1-42}$ was more abundant and formed "diffuse" plaques that could not be easily enumerated (see FIG. 5). For these slides a computer-assisted method (C.A.S.T. stereology system) was used to estimate the area of entorhinal cortex occupied by $A\beta^{1-42}$. This area was expressed as a percent of the total area of cortex on the slide. The areas occupied by neuritic and diffuse plaques were counted separately. The computer-driven microscope stage assured random (unbiased) evaluation of the tissue sections. The volume % of entorhinal cortex occupied by $A\beta^{1-42}$ (both diffuse and neuritic) is compared to the number of CCR1-positive plaques in a sister section of entorhinal cortex in FIG. 7.

FIG. 6 shows that the average number of CCR1-positive dystrophic neurites in the hippocampus increases as a function of CDR score in Alzheimer's disease. The number of positive structures in early Alzheimer's disease (CDR 0.5) is increased above control (COR 0) levels. Although the differences between control and Alzheimer's disease groups did not become statistically significant until group CDR 2, these expression patterns support the conclusion that CCR1 is upregulated in dystrophic neuronal processes even at very early stages of Alzheimer's disease. Note that the number of $A\beta^{1-40}$ plaques do not rise until late in the disease. CCR1 expression in brain tissue may thus be considered a relatively early indicator of Alzheimer's disease.

Figure 7:
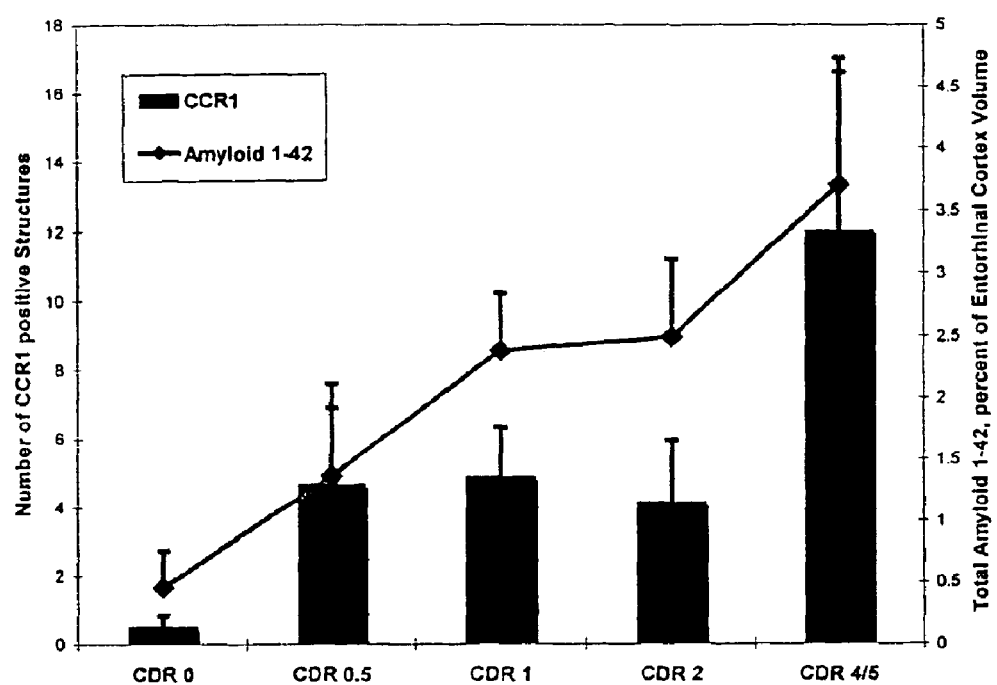
FIG. 7 is a graph showing the relationship between CCR1 and $A\beta^{1-42}$ by CDR score.

The correlation between number of CCR1-positive plaques in entorhinal cortex and the amount of $A\beta^{1-42}$ is shown in FIG. 7. In general, CCR1 levels in entorhinal cortex rise as the disease state increases; however, the area sampled is much smaller than the area sampled in FIG. 6. Note, however, that $A\beta^{1-42}$ levels rise early in the disease.

EXAMPLE 11

Assessment of Brain Availability, Using a $^{14}$C-Labeled Tracer

Figure 8:
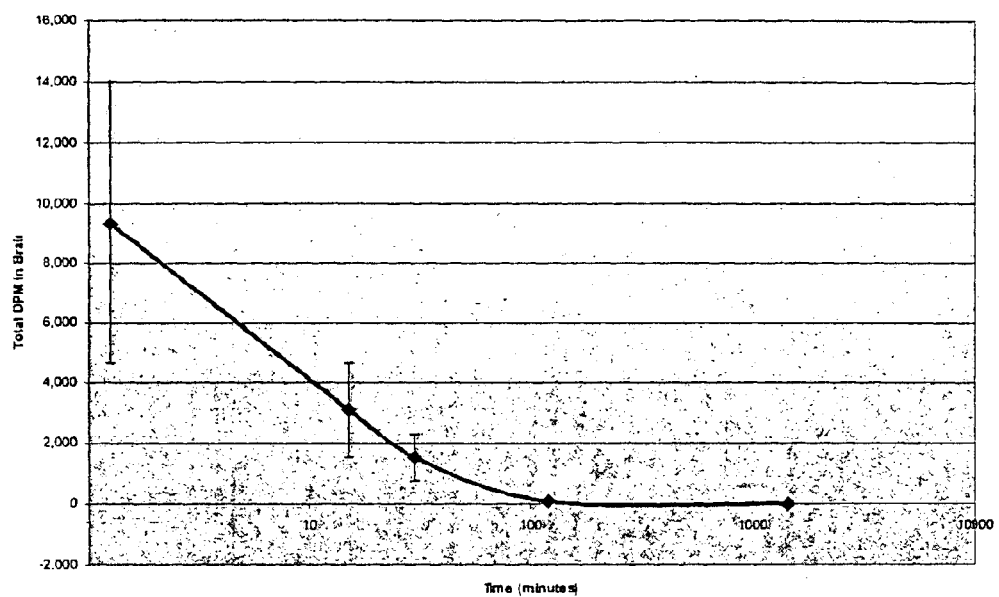
FIG. 8 is a graph demonstrating the decrease in total brain radioactivity over time.

A $^{14}$C analogue of 1-(5-chloro-2-{2-[(2R)-4-(4-fluorobenzyl)-2-methylpiperazin-1-yl]-2-oxoethoxy}phenyl)urea was prepared and used for pharmacokinetic studies of brain availability. Mice were injected i.v. through cannulated jugular veins with the analogue at 36 mg/kg containing 334,000 dpm per dose. Mice (in groups of four) were sacrificed at 1, 15, 30, 120, and 1440 minutes after injection by $CO_2$ inhalation followed by intra-cardiac puncture for removal of whole blood. The chest was then opened and mice were perfused through the heart with phosphate buffered saline for five minutes to remove residual radioactive drug from the blood compartment. The brains were then removed, weighed, and sampled for amount of radioactivity in two separate pieces of cerebral cortex. The radioactivity levels per mg of tissue in the two samples were averaged and the data were normalized to total brain weight, as illustrated in FIG. 8. The bars represent the standard error (n=4 mice per time point). In particular, the graph in FIG. 8 shows that the total number of disintegrations per minute (DPM) for $^{14}$C analogue in whole mouse brain decreases to negligible levels by two hours after injection. At the 1-minute time point, calculations show that, on average, about 3% of the injected dose is found in whole mouse brain (average weight of 450 g).

Plasma samples prepared from the whole blood removed from the mice were also analyzed for radioactive content.

Figure 9:
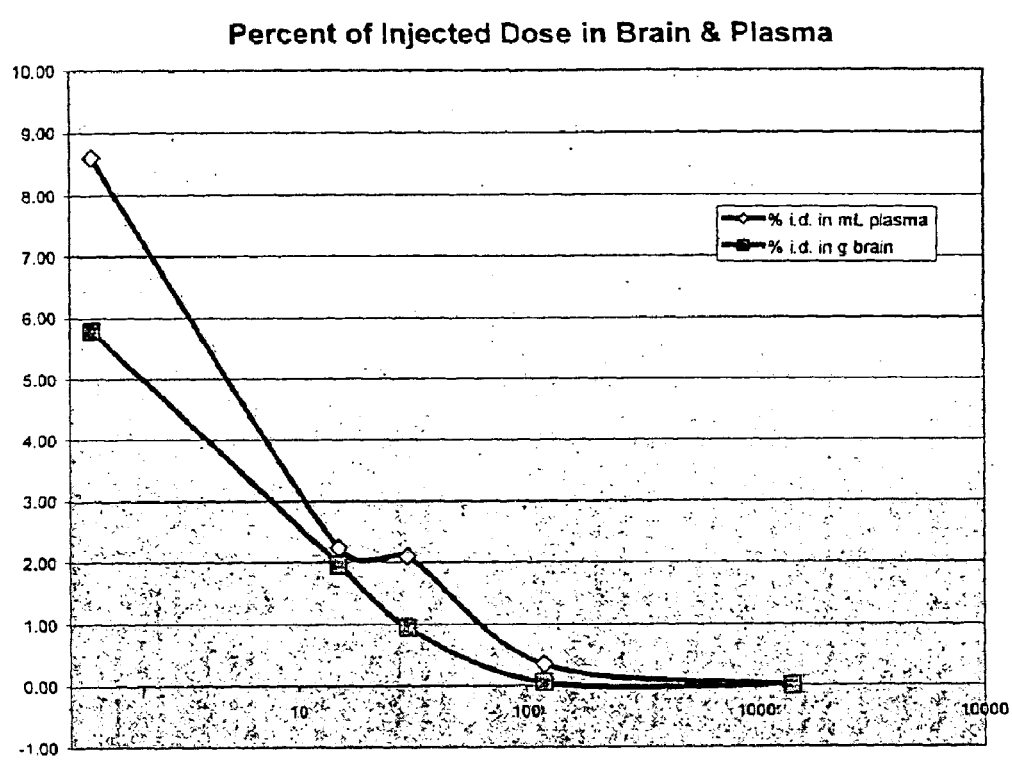
FIG. 9 is a graph showing the percent of injected dose in brain and plasma.

The amount of radioactivity in equal volumes of brain and plasma was compared over time as a percent of injected dose, as illustrated in FIG. 9. The % of injected dose (i.d.) found per mL of plasma also declines over time, reaching negligible levels after two hours. For comparison to brain levels, the total number of DPM per brain were normalized to a gram of brain weight and expressed as a percentage of the i.d. per gram of brain tissue. Note that mouse brains weigh on average about 450 mg so that the % of i.d. in 1 g of mouse brain shown in the graph overestimates the real value by about two-fold. It is clear that the levels of the analogue in the brain fall in concert with plasma levels. Although the analogue is lipophilic, normal mouse brain does not appear to be a depot site for the CCR1 antagonist.

EXAMPLE 12

CCR1 Expression in Other Neurodegenerative Diseases

Materials and Methods

Histologic samples of autopsy brain tissue from a total of 29 cases from seven different neurodegenerative diseases (other than pure Alzheimer's disease) were obtained and studied for CCR1 content. Slides were immunostained with antibodies against CCR1 as described in Example 10 above and reviewed under blinded conditions with respect to the specific neurodegenerative disease. Subsequently, sister sections were double-labeled with antibodies against CCR1 (DAB as chromogen) and $A\beta^{1-42}$ (Vector Red™ as chromogen). The diseases examined are listed below:

| | |
|---|---|
| Parkinson's disease (PD) | 6 cases |
| Parkinsonian dementia of Guam | 3 cases |
| Congophilic angiopathy | 4 cases |
| Multi-infarct dementia (MID) | 4 cases |
| Diffuse Lewy body dementia (DLBD) | 4 cases |
| Pick's disease | 4 cases |
| Progressive supranuclear palsy (PSP) | 4 cases |

The stained slides were graded for CCR1 and $A\beta^{1-42}$ content using a histologic scale of 0 to 4, with 0 being absence of staining, 0.5 indicating rare expression, and grades 1 through 4 indicating increasing levels of expression with 4 being highly abundant.

Results

All six cases of Parkinson's disease and all three cases of Parkinsonian dementia of Guam were negative for CCR1. CCR1-positive plaque-like structures, similar to those found in Alzheimer's disease, were observed in all 4 cases of congophilic angiopathy, in 3 of the 4 cases of DLBD, in 2 out of the 4 cases of PSP, and in 1 out of the 4 cases of both MID and Pick's disease.

Figure 10:
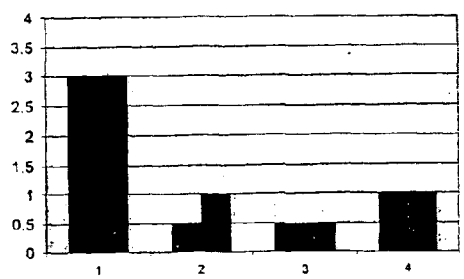
FIG. 10 are graphs showing CCR1 expression in other neurodegenerative diseases.
Figure 10:
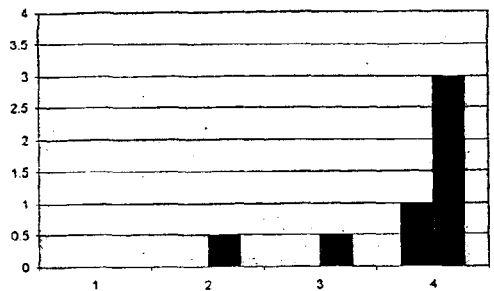
Figure 10:
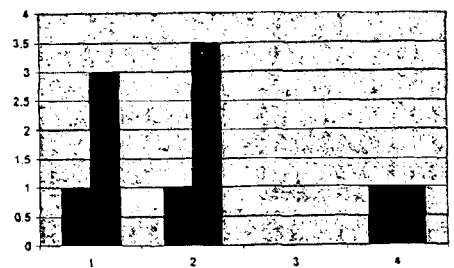
Figure 10:
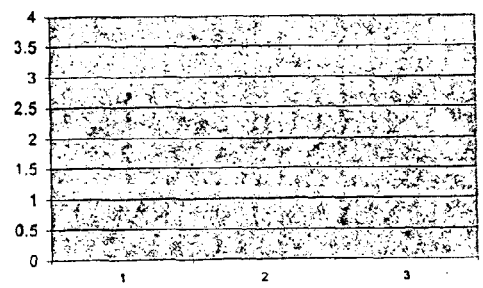
Figure 10:
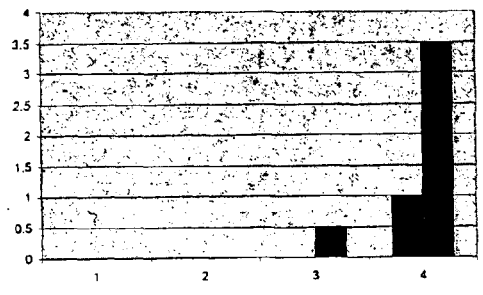
Figure 10:
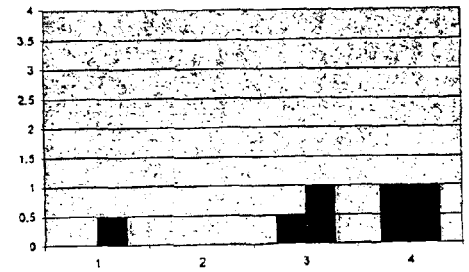

Double-labeling studies confirmed the assumption that these CCR1-positive plaque-like structures were associated with $A\beta^{1-42}$, as was found in pure cases of Alzheimer's disease (Example 10). FIG. 10 shows the results of the pathological evaluations in graphic form for all the diseases except for Parkinson's (which was negative for CCR1 in brain). Basically, CCR1 expression was never found in brain tissue samples unless $A\beta^{1-42}$-positive neuritic plaques were also present.

After the code was broken, it was found that the one case of Pick's disease showing CCR1 expression also carried the diagnosis of Alzheimer's disease. The two PSP cases with CCR1 were also diagnosed with concurrent Alzheimer's disease. Congophilic angiopathy and DLBD are diseases that are closely associated with Alzheimer's disease pathology. Therefore, it is not surprising that they would also have high levels of CCR1 expression in association with $A\beta^{1-42}$. In elderly populations it is often the case that Alzheimer's disease pathology will overlay other disease processes. This was found in one of the four MID cases. These results suggests that CCR1 is a marker that is closely associated with Alzheimer's disease pathology (specifically, $A\beta^{1-42}$-positive neuritic plaques) regardless of other concurrent pathological processes that may be present in brain. As such, it is likely to be highly specific for Alzheimer's disease pathology and therefore may be useful as a diagnostic surrogate marker of disease progression.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of diagnosing Alzheimer's disease in a human patient which comprises:

administering to a patient in need of such diagnosis a compound according to of formula (I):

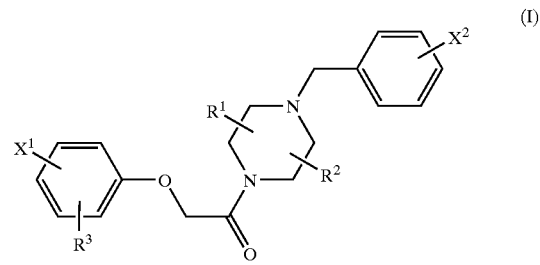

wherein:

$X^1$ and $X^2$ are each independently halo;

$R^1$ and $R^2$ are each independently hydrogen or alkyl; and $R^3$ is hydrogen, amino, monoalkylamino, dialkylamino, monoaralkylamino, alkylcarbonylanmino, alkenylcarbonylamino, haloalkylcarbonylamino, arylcarbonylamino, alkoxyalkylcarbonylamino, alkoxycarbonylalkylcarbonylamino, glycinamido, monoalkylglycinamido, arylcarbonylglycinamido, aminocarbonylglycinamido, (aminocarbonyl)(alkyl)glycinamido, (alkoxyalkylcarbonyl)glycinamido, ureido, monoalkylureido, monoarylureido, monoaralkylureido, or alaninamido;

and wherein either one of $X^1$ or $X^2$ is selected from the group of $^{123}$I, $^{125}$I, $^{128}$I, $^{131}$I, $^{75}$Br, $^{76}$Br, $^{80}$Br and $^{18}$F; or wherein one of the carbon atoms in the compound is $^{11}$C;

or a pharmaceutically acceptable salt thereof, and measuring the radioactivity arising from the administration of the compound to said patient either by using a gamma camera or by positron emission tomography (PET).

2. A method of diagnosing Alzheimer's disease in a human patient which comprises administering to said patient in need of such diagnosis a compound according to formula (II):

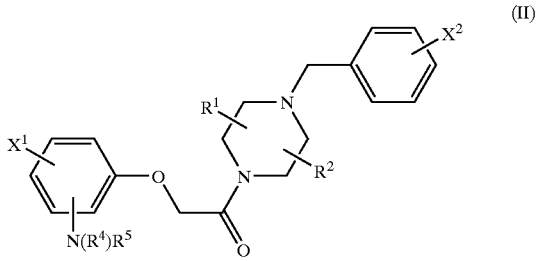

(II)

wherein $X^1$ and $X^2$ are each independently halo;

$R^1$ and $R^2$ are each independently hydrogen or alkyl; and $R^4$ is hydrogen; and $R^5$ is a group having a radical containing a chelator capable of binding a radioactive metal atom selected from the group of $^{99m}Tc$, $^{186}Re$ and $^{188}Re$;

or as a complex with $^{99m}Tc$, $^{186}Re$ and $^{188}Re$;

or a pharmaceutically acceptable salt thereof; and measuring the radioactivity arising from the administration of the compound to said patient either by using a gamma camera or by position emission tomography (PET).

3. A method according to claim 1, wherein said compound binds to chemokine reseptor CCR1 and passes the blood-brain barrier.

4. A method according to claim 2, wherein said compound binds to chemokine receptor CCR1 and passes the blood-brain barrier.

5. A method according to claim 1, wherein $R^1$ is methyl at the 2-position of the piperazinyl radical and $R^2$ is methyl at the 5-position of the piperazinyl radical.

6. A method according to claim 2, wherein $R^1$ is methyl at the 2-position of the piperazinyl radical and $R^2$ is methyl at the 5-position of the piperazinyl radical.

7. A method according to claim 1, wherein $R^1$ is methyl at the 2-position of the piperazinyl radical and $R^2$ is hydrogen.

8. A method according to claim 2, wherein $R^1$ is methyl at the 2-position of the piperazinyl radical and $R^2$ is hydrogen.

9. A method of claim 1, wherein $X^1$ is chloro at the 4-position of the phenyl radical and $X^2$ is a $^{18}F$ atom at the 4-position of the phenyl radical.

10. A method of claim 2, wherein said chelator is of formula (III):

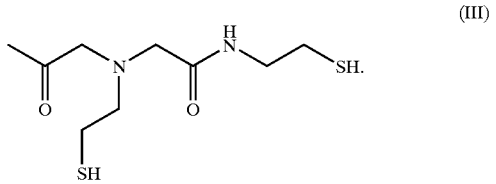

(III)

11. A method of claim 2, wherein said chelator is of formula (IV):

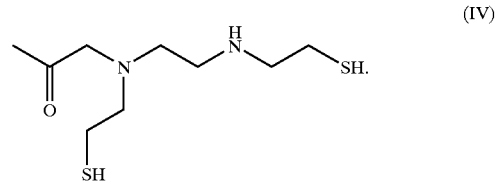

(IV)

12. A method of claim 10, wherein in group $R^5$ a linker moiety is present between said chelator and the reminder of the compound.

13. A method of claim 11, wherein in group $R^5$ a linker moiety is present between said chelator and the reminder of the compound.

14. A method of claim 12, wherein the linker moiety is —C(O)—CH$_2$N(H).

15. A method of claim 13, wherein the linker moiety is —C(O)—CH$_2$—N(H).

16. A method according to claim 1, wherein said compound is a monochloride salt.

17. A method according to claim 2, wherein said compound is a monochloride salt.

18. A method according to claim 1, wherein said compound is a dichloride salt.

19. A method according to claim 2, wherein said compound is a dichloride salt.

20. A method according to claim 1, wherein $X^1$ and $X^2$ are each independently bromo, chloro, iodo or fluoro;

$R^1$ and $R^2$ are each independently hydrogen, methyl, ethyl, n-propyl, 1-methylethyl, n-butyl, 1,1-dimethylethyl, n-pentyl, or n-heptyl; and $R^3$ is hydrogen, amino, methylamino, ethylamino, propylamino, dimethylamino, methylethylamino, diethylamino, dipropylamino, ethylpropylamino, benzylamino, (3,4,5-trimethoxybenzyl)amino, (4-chlorobenzyl)amino, acetylamino, ethylcarbonylamino, n-propylcarbonylamino, ethenylcarbonylamino, prop-2-enylcarbonylamino, but-2-enylcarbonylamino, trifluoromethylcarbonylamino, trifluoromethylcarbonylamino, 2-bromoethylcarbonylamino, (4-methoxyphenyl)carbonylamino, (4-fluorophenyl)carbonylamino, (4-chlorophenyl)carbonylamino, alkoxyalkylcarbonylamino wherein the alkoxy and alkyl portion each have 1 to 8 carbon atoms, ethoxycarbonylmethylcarbonylamino, methoxycarbonylmethylcarbonylamino, (2-ethoxycarbonylethyl)carbonylamino, (2-methoxycarbonylethyl)carbonylamino, glycinamido, —N(H)—C(O)—CH$_2$—N(H)R$_a$, phenylcarbonylglycinamido, (4-fluoro-3-trifluoromethylphenyl)carbonylglycinamido, (4-fluorophenyl)carbonylglycinamido, aminocarbonylglycinamido, —N(H)—C(O)—CH$_2$—N(R$_a$)—C(O)—NH$_2$, (methoxyacetyl)glycinamido, (ethoxyacetyl)glycinamido, ureido, —N(H)—C(O)—N(H)R$_a$, —N(R$_a$)—C(O)—NH$_2$—N(H)—C(O)—N(H)R$_b$, —N(R$_b$)—C(O)—NH$_2$, —N(H)—C(O)—N(H)R$_d$, —N(R$_d$)—C(O)—NH$_2$, or alaninamido;

$R_a$ is an alkyl radical having from one to eight carbon atoms;

$R_b$ is a phenyl or naphthyl radical which is optionally substituted by one or more substituents selected from the group consisting of bromo, chloro, iodo or fluoro, alkyl having from one to eight carbon atoms, alkoxy having from one to eight carbon atoms, haloalkyl having from one to eight carbon atoms, haloalkoxy having from one to eight carbon atoms, nitro, amino, —N(H)$R_a$, and —N($R_a$)$R_a$ where each $R_a$ is independently alkyl having from one to eight carbon atoms, and $R_d$ is an aralkyl group in which the alkyl portion has one to eight carbon atoms and the aryl portion is $R_b$;

wherein either one of $X^1$ or $X^2$ is selected from the group of $^{123}$I; $^{125}$I, $^{128}$I, $^{131}$I, $^{75}$Br, $^{76}$Br, $^{80}$Br and $^{18}$F or one of the carbon atoms in the compound is $^{11}$C.

21. A method according to claim 1, wherein
$X^1$ and $X^2$ are each independently bromo, chloro, iodo or fluoro; and
$R^1$ and $R^2$ are each independently hydrogen, methyl, ethyl, n-propyl, 1-methylethyl, n-butyl, 1,1-dimethylethyl, n-pentyl, or n-heptyl.

22. A method according to claim 2, wherein in group $R^5$ a linker moiety is present between said chelator and the reminder of the compound, wherein the linker moiety is an alkyl radical having one to ten carbon atoms, wherein the alkyl radical optionally contains one to ten —C(O)-groups, one to ten —C(O)N(R)-groups, one to ten —N(R)C(O)-groups, one to ten —N(R)-groups, one to ten —N(R)$_2$ groups, one to ten hydroxy groups, one to ten —C(O)OR-groups, one to ten oxygen atoms, one to ten sulfur atoms, one to ten nitrogen atoms, one to ten halogen atoms, and one to ten aryl groups.

23. A method according to claim 10, wherein in group $R^5$ a linker moiety is present between said chelator and the reminder of the compound, wherein the linker moiety is an alkyl radical having one to ten carbon atoms, wherein the alkyl radical optionally contains one to ten —C(O)—groups, one to ten —C(O)N(R)-groups, one to ten —N(R)C(O)— groups, one to ten —N(R)—groups, one to ten —N(R)$_2$ groups, one to ten hydroxy groups, one to ten —C(O)OR-groups, one to ten oxygen atoms, one to ten sulfur atoms, one to ten nitrogen atoms, one to ten halogen atoms, and one to ten aryl groups.

24. A method according to claim 11, wherein in group $R^5$ a linker moiety is present between said chelator and the reminder of the compound, wherein the linker moiety is an alkyl radical having one to ten carbon atoms, wherein the alkyl radical optionally contains one to ten —C(O)—groups, one to ten —C(O)N(R)-groups, one to ten —N(R)C(O)— groups, one to ten —N(R)-groups, one to ten —N(R)$_2$ groups, one to ten hydroxy groups, one to ten —C(O)OR-groups, one to ton oxygen atoms, one to ton sulfur atoms, one to ten nitrogen atoms, one to ten halogen atoms and one to ten aryl groups.

25. A method according to claim 1 wherein the radioactive dose administered to said patient is 1 to 100 mCi per application.

26. A method according to claim 2, wherein the radioactive dose administered to said patient is 1 to 100 mCi per application.

27. A method according to claim 3, wherein the radioactive dose administered to said patient is 1 to 100 mCi per application.

28. A method according to claim 4, wherein the radioactive dose administered to said patient is 1 to 100 mCi per application.

29. A method according to claim 1, wherein said compound is selected from the group consisting of the following:
1-(5-chloro-2-{2-[(2R)-4-(4-fluoro-$^{18}$F-benzyl)-2-methylpiperazin-1-yl]-2-oxoethoxy}phenyl)urea;
1-(2-{2-[(2R)-4-(4-fluorobenzyl)-2-methylpiperazin-1-yl]-2-oxoethoxy}-5-iodo-$^{123}$I-phenyl)urea;
2-(2-amino-4-chlorophenoxy)-1-[(2RS,5RS)-4-(4-fluoro-$^{18}$F-benzyl)-2,5-dimethylpiperazin-1-yl]ethan-1-one;
2-(2-amino-4-chlorophenoxy)-1-[(2SR,5SR)-4-(4-fluoro-$^{18}$F-benzyl)-2,5-dimethylpiperazin-1-yl]ethan-1-one;
2-(2-amino-4-chlorophenoxy)-1-[(2RS,5SR)-4-(4-fluoro-$^{18}$F-benzyl)-2,5-dimethylpiperazin-1-yl]ethan-1-one;
2-(2-amino-4-chlorophenoxy)-1-[(2RS,5SR)-4-(4-fluoro-$^{18}$F-benzyl)-2,5-dimethylpiperazin-1-yl]ethan-1-one;
2-[4-chloro-2-(diethylamino)phenoxy]-1-[(2SR,5RS)-4-(4-fluoro-$^{18}$F-benzyl)-2,5-dimethylpiperazin-1-yl]ethan-1-one;
2-[4-chloro-2-(diethylamino)phenoxy]-1-[(2RS,5RS)-4-(4-fluoro-$^{18}$F-benzyl)-2,5-dimethylpiperazin-1-yl]ethan-1-one;
2-[4-chloro-2-(diethylamino)phenoxy]-1-[(2SR,5SR)-4-(4-fluoro-$^{18}$F-benzyl)-2,5-dimethylpiperazin-1-yl]ethan-1-one;
2-[4-chloro-2-(diethylamino)phenoxy]-1-[(2RS,5SR)-4-(4-fluoro-$^{18}$F-benzyl)-2,5-dimethylpiperazin-1-yl]ethan-1-one;
1-(5-chloro-2-{2-[(2RS,5SR)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2SR,5SR)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2SR,5RS)-4-(4-fluoro-$^{18}$F-benzyl)-2,5-dimethylpiperazin-1-yl]-2-oxoethoxy}phenyl)-3-(2,4-dichlorophenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)urea;
1-(5-chloro-2-{2-[(2SR,5SR)-4-(4-fluoro-$^{18}$F-benzyl)-2,5-dimethylpiperazin-1-yl]-2-oxoethoxy}phenyl)urea;
1-(5-chloro-2-{2-[(2SR,5RS)-4-(4-fluoro-$^{18}$F-benzyl)-2,5-dimethylpiperazin-1-yl]-2-oxoethoxy} phenyl)urea;
1-(5-chloro-2-{2[(2SR,5SR)-4-(4-fluoro-$^{18}$F-benzyl) 2,5-dimethylpiperazin-1-yl]-2-oxoethoxy}phenyl)urea;
1-(5-chloro-2-{2-[(2RS,5SR)-4-(4-fluoro-$^{18}$F-benzyl)-2,5-dimethylpiperazin-1-yl]-2-oxoethoxy}phenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)urea;
1-(5-chloro-2-{2-[(2RS,5RS)-4-(4-fluoro-$^{18}$F-benzyl)-2,5-dimethylpiperazin-1-yl]-2-oxoethoxy}phenyl)urea;
1-(5-chloro-2-{2-[(2SR,5RS)-4-(4-fluoro-$^{18}$F-benzyl)2,5-dimethylpiperazin-1-yl]-2-oxoethoxy}phenyl)urea;
1-[(2SR,5RS)-4-(4-fluoro-$^{18}$F-benzyl])-2,5-dimethylpiperazin-1-yl]-2-(2-isopentylamino-4-chlorophenoxy)ethan-1-one;
1-[(2SR,5RS)-4-(4-fluoro-$^{18}$F-benzyl)-2,5-dimethylpiperazin-1-yl]-2-(2-isopentylamino-4-chlorophenoxy)ethan-1-one;
1-[(2SR,5RS)-4-(4-fluoro-$^{18}$F-benzyl)-2,5-dimethylpiperazin-1-yl]-2-(2-isopentylamino-4-chlorophenoxy)ethan-1-one;
N-(5-chloro-2-{2-[(2SR,5RS)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-methylpropanamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(methoxy)acetamide
N-(5-chloro-2-{2-[(2SR,5RS)-4-(4-fluoro-$^{18}$F-benzyl)-2,5-dimethylpiperazin-1-yl]-2-oxoethoxy}phenyl)-2-(methoxy)acetamide N-(5-chloro-2-{2-[(2SR,5RS)-4-(4-fluoro-$^{18}$F-benzyl)-2,5-dimethylpiperazin-1-yl]-2-oxoethoxy}phenyl)-2-(methoxy)acetamide N-(5-chloro-2-{2-[(2RS,5SR)-4-(4-fluoro-$^{18}$F-benzyl)-2,5-dimethylpiperazin-1-yl]-2-oxoethoxy} phenyl)-2-(methoxy)acetamide;

(E)-N-5-chloro-2-{2-[(2RS,5SR)-4-(4-fluoro-$^{18}$F-benzyl)-2,5-dimethylpiperazin-1-yl]-2-oxoethoxy} phenyl)-2-butenamide;

(E)-N-(5-chloro-2-{2-[(2SR,5SR)-4-(4-fluoro-$^{18}$F-benzyl)-2,5-dimethylpiperazin-1-yl]-2-oxoethoxy} phenyl)-2-butenamide;

(E)-N-(5-chloro-2-{2-[(2RS,5RS)-4-(4-fluoro-$^{18}$F-benzyl)-2,5-dimethylpiperazin 1-yl]-2-oxoethoxy}phenyl)-2-butenamide;

(E)-N-(5-chloro-2-{2-[(2SR,5RS)-4-(4-fluoro-$^{18}$F-benzyl) 2,5-dimethylpiperazin-1-yl]-2-oxoethoxy}phenyl)-2-butenamide;

methyl N-(5-chloro-2-{2-[(2SR,5RS)-4-(4-fluoro-$^{18}$F-benzyl)-2,5-dimethylpiperazin-1-yl]-2-oxoethoxy}phenyl)succinamate;

methyl N-(5-chloro-2-{2-[(2RS,5RS)-4-(4-fluoro-$^{18}$F-benzyl)-2,5-dimethylpiperazin-1-yl]-2-oxoethoxy}phenyl)succinamate;

methyl N-(5-chloro-2-{2-[(2SR,5SR)-4-(4-fluoro-$^{18}$F-benzyl)-2,5-dimethylpiperazin-1-yl]-2-oxoethoxy}phenyl)succinamate;

methyl N-(5-chloro-2-{2-[(2RS,5SR)-4-(4-fluoro-$^{18}$F-benzyl)-2,5-dimethylpiperazin 1-yl]-2-oxoethoxy}phenyl)succinamate;

ethyl N-(5-chloro-2-{2-[(2SR,5RS)-4-(4-fluoro-$^{18}$F-benzyl)-2,5-dimethylpiperazin 1-yl]-2-oxoethoxy}phenyl)succinamate;

ethyl N-(5-chloro-2-{2-[(2RS,5RS)-4-(4-fluoro-$^{18}$F-benzyl)-2,5-dimethylpiperazin-1-yl]-2-oxoethoxy}phenyl)succinamate;

ethyl N-(5-chloro-2-{2-[(2SR,5SR)-4-(4-fluoro-$^{18}$F-benzyl)-2,5-dimethylpiperazin-1-yl]-2-oxoethoxy}phenyl)succinamate;

ethyl N-(5-chloro-2-{2-[(2RS,5SR)-4-(4-fluoro-$^{18}$F-benzyl)-2,5-dimethylpiperazin-1-yl]-2-oxoethoxy}phenyl)succinamate;

N-(5-chloro-2-{2-[(2SR,5RS)-4-(4-fluoro-$^{18}$F-benzyl)-2,5-dimethylpiperazin-1-yl]-2-oxoethoxy}phenyl)acetamide;

N-(5-chloro-2-{2-[(2RS,5RS)-4-(4-fluoro-$^{18}$F-benzyl)-2,5-dimethylpiperazin-1-yl]-2-oxoethoxy}phenyl)acetamide;

N-5-chloro-2-{2-[(2SR,5SR)-4-(4-fluoro-$^{18}$F-benzyl)-2,5-dimethylpiperazin-1-yl]-2-oxoethoxy}phenyl)acetamide;

N-(5-chloro-2-{2-[(2RS,5SR)-4-(4-fluoro-$^{18}$F-benzyl)-2,5-dimethylpiperazin-1-yl]-2-oxoethoxy}phenyl)acetamide;

N-(5-chloro-2-{2[(2SR,5RS)-4-(4-fluoro-$^{18}$F-benzyl)-2,5-dimethylpiperazin-yl]-2-oxoethoxy}phenyl)propanamide;

N-(5-chloro-2-{2[(2SR,5SR)-4-(4-fluoro-$^{18}$F-benzyl)-2,5-dimethylpiperazin-yl]-2-oxoethoxy}phenyl)propanamide;

N-(5-chloro-2-{2[(2SR,5RS)-4-(4-fluoro-$^{18}$F-benzyl)-2,5-dimethylpiperazin-yl]-2-oxoethoxy}phenyl)propanamide;

N-(5-chloro-2-{2[(2RS,5SR)-4-(4-fluoro-$^{18}$F-benzyl)-2,5-dimethylpiperazin-yl]-2-oxoethoxy}phenyl)propanamide;

N-(5-chloro-2-{2[(2SR,5RS)-4-(4-fluoro-$^{18}$F-benzyl)-2,5-dimethylpiperazin-yl]-2-oxoethoxy}phenyl)-3-fluorobenzamide;

N-(5-chloro-2-{2[(2RS,5SR)-4-(4-fluoro-$^{18}$F-benzyl)-2,5-dimethylpiperazin-yl]-2-oxoethoxy}phenyl)-3-fluorobenzamide;

N-(5-chloro-2-{2[(2SR,5RS)-4-(4-fluoro-$^{18}$F-benzyl)-2,5-dimethylpiperazin-yl]-2-oxoethoxy}phenyl)-3-fluorobenzamide;

N-(5-chloro-2-{2[(2SR,5RS)-4-(4-fluoro-$^{18}$F-benzyl)-2,5-dimethylpiperazin-yl]-2-oxoethoxy}phenyl)-3-fluorobenzamide;

1-(5-chloro-2-{2-[(2SR,5RS)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2SR,5SR)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2RS,5SR)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2SR,5RS)-4-(4-fluoro-$^{18}$F-benzyl)-2,5-dimethylpiperazin-1-yl]-2-oxoethoxy}phenyl)-3-(p-tolyl)urea;

1-(5-chloro-2-{2-[(2SR,5RS)-4-(4-fluoro-$^{18}$F-benzyl)-2,5-dimethylpiperazin-1-yl]-2-oxoethoxy}phenyl)-3-ethylurea;

1-(5-chloro-2-{2-[(2RS,5RS)-4-(4-fluoro-$^{18}$F-benzyl)-2,5-dimethylpiperazin-1-yl]-2-oxoethoxy}phenyl)-3-ethylurea;

1-(5-chloro-2-{2-[(2SR,5SR)-4-(4-fluoro-$^{18}$F-benzyl)-2,5-dimethylpiperazin-1-yl]-2-oxoethoxy}phenyl)-3-ethylurea;

1-(5-chloro-2-{2-[(2RS,5SR)-4-(4-fluoro-$^{18}$F-benzyl)-2,5-dimethylpiperazin-1-yl]-2-oxoethoxy}phenyl)-3-ethylurea;

1-benzyl-3-(5-chloro-2-{2-[(2SR,5RS)-4-(4-fluoro-$^{18}$F-benzyl)-2,5-dimethylpiperazin-1-yl]-2-oxoethoxy}phenyl)urea;

1-benzyl-3-(5-chloro-2-{2-[(2RS,5SR)-4-(4-fluoro-$^{18}$F-benzyl)-2,5-dimethylpiperazin-1-yl]-2-oxoethoxy}phenyl)urea;

1-benzyl-3-(5-chloro-2-{2-[(2RS,5RS)-4-(4-fluoro-$^{18}$F-benzyl)-2,5-dimethylpiperazin-1-yl]-2-oxoethoxy}phenyl)urea;

1-benzyl-3-(5-chloro-2-{2-[(2RS,5SR)-4-(4-fluoro-$^{18}$F-benzyl)-2,5-dimethylpiperazin-1-yl]-2-oxoethoxy}phenyl)urea;

1-(5-chloro-2-{2-[(2RS,5SR)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2SR,5SR)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2RS,5RS)-4-(4-fluoro-$^{18}$F-benzyl)-2,5-dimethylpiperazin-1-yl]-2-oxoethoxy}phenyl)-3-(4-nitrophenyl)urea;

1-(5-chloro-2-{2-[(2SR,5RS)-4-(4-fluoro-$^{18}$F-benzyl)-2,5-dimethylpiperazin-1-yl]-2-oxoethoxy}phenyl)-3-(4-nitrophenyl)urea;

2-(2-benzylamino-4-chlorophenoxy)-1-[(2SR,5RS)-4-(4-fluoro-$^{18}$F-benzyl)-2,5-dimethylpiperazin-1-yl]ethan-1-one;

2-(2-benzylamino-4-chlorophenoxy)-1-[(2RS,5RS)-4-(4-fluoro-$^{18}$F-benzyl)-2,5-dimethylpiperazin-1-yl]ethan-1-one;

2-(2-benzylamino-4-chlorophenoxy)-1-[(2SR,5SR)-4-(4-fluoro-$^{18}$F-benzyl)-2,5-dimethylpiperazin-1-yl]ethan-1-one;

2-(2-benzylamino-4-chlorophenoxy)-1-[(2RS,5SR)-4-(4-fluoro-$^{18}$F-benzyl)-2,5-dimethylpiperazin-1-yl]ethan-1-one;

N-(5-chloro-2-{2-[(2RS,5SR)-4-(4-fluoro-$^{18}$F-benzyl)-2,5-dimethylpiperazin-1-yl]-2-oxoethoxy}phenyl)glycinamide;

N-(5-chloro-2-{2-[(2RS,5RS)-4-(4-fluoro-$^{18}$F-benzyl)-2,5-dimethylpiperazin-1-yl]-2-oxoethoxy}phenyl)glycinamide;

N-(5-chloro-2-{2-[(2SR,5SR)-4-(4-fluoro-$^{18}$F-benzyl)-2,5-dimethylpiperazin-1-yl]-2-oxoethoxy}phenyl)glycinamide;

N-(5-chloro-2-{2-[(2RS,5RS)-4-(4-fluoro-$^{18}$F-benzyl)-2,5-dimethylpiperazin-1-yl]-2-oxoethoxy}phenyl)glycinamide;
1-(5-chloro-2-{2-[(2R)-4-(4-fluoro-$^{18}$F-benzyl)-2-methylpiperazin-1-yl]-2-oxoethoxy}phenyl)urea,
1-(5-chloro-2-{2 [(2S)-(4-fluoro-$^{18}$F-benzyl)-2,5-methylpiperazin-1-yl]-2-oxoethoxy}phenyl)urea;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(methylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(methylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(methylamino)acetamide;
2-bromo-N-(5-chloro-2-{(2SR,5RS)-4-(4-fluoro-$^{18}$F-benzyl)-2,5-dimethylpiperazin-1-yl]-2-oxoethoxy}phenyl)acetamide;
2-bromo-N-(5-chloro-2-{(2SR,5RS)-4-(4-fluoro-$^{18}$F-benzyl)-2,5-dimethylpiperazin-1-yl]-2-oxoethoxy}phenyl)acetamide;
2-bromo-N-(5-chloro-2-{(2SR,5RS)-4-(4-fluoro-$^{18}$F-benzyl)-2,5-dimethylpiperazin-1-yl]-2-oxoethoxy}phenyl)acetamide;
2-bromo-N-(5-chloro-2-{(2SR,5RS)-4-(4-fluoro-$^{18}$F-benzyl)-2,5-dimethylpiperazin-1-yl]-2-oxoethoxy}phenyl)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(ureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(ureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(ureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(1-methylureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(1-methylureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(1-methylureido)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(1-methylureido)acetamide;
(2RS)-N-(5-chloro-2-{2-[(2SR,5SR)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2RS,5SR)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2SR,5SR)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2SR,5SR)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2RS,5SR)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2RS,5SR)-4-(4-fluoro-$^{18}$F-benzyl)-2,5-dimethylpiperazin-1-yl]-2-oxoethoxy}phenyl)-2-aminopropanamide;
(2RS)-N-(5-chloro-2-{2-[(2SR,5RS)-4-(4-fluoro-$^{18}$F-benzyl)-2,5-dimethylpiperazin-1-yl]-2-oxoethoxy}phenyl)-2-aminopropanamide;
(2SR)-N-(5-chloro-2-{2-[(2SR,5RS)-4-(4-fluoro-$^{18}$F-benzyl)-2,5-dimethylpiperazin-1-yl]-2-oxoethoxy}phenyl)-2-aminopropanamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(2,4-difluorobenzoylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(2,4-difluorobenzoylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(2,4-difluorobenzoylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(2,4-difluorobenzoylamino)acetamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(methoxyacetylamino)acetamide;
N-(5-chloro-2-{2-[(2RS,5RS)-4-(4-fluoro-$^{18}$F-benzyl)-2,5-dimethylpiperazin-1-yl]-2-oxoethoxy}phenyl)-2-(methoxyacetylamino)acetamide;
N-(5-chloro-2-{2-[(2SR,5SR)-4-(4-fluoro-$^{18}$F-benzyl)-2,5-dimethylpiperazin-1-yl]-2-oxoethoxy}phenyl)-2-(methoxyacetylamino)acetamide;
N-(5-chloro-2-{2-[(2RS,5SR)-4-(4-fluoro-$^{18}$F-benzyl)-2,5-dimethylpiperazin-1-yl]-2-oxoethoxy}phenyl)-2-(methoxyacetylamino)acetamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(2-iodobenzoylamino)acetamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(2-iodobenzoylamino)acetamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(2-iodobenzoylamino)acetamide;
N-(5-chloro-2-{2-[(2SR,5RS)-4-(4-fluoro-$^{18}$F-benzyl)-2,5-dimethylpiperazin-1-yl]-2-oxoethoxy}phenyl)-2-(2-iodobenzoylamino)acetamide;
N-(5-chloro-2-{2-[(2R)-4-(4-fluoro-$^{18}$F-benzyl)-2-methylpiperazin-1-yl]-2-oxoethoxy}phenyl)glycinamide;
N-(5-chloro-2-{2-[(2R)-4-(4-fluoro-$^{18}$F-benzyl)-2-methylpiperazin-1-yl]-2-oxoethoxy}phenyl)glycinamide; and
mono- and dichloride salts thereof.

30. A method according to claim 1, wherein said compound is selected from the group consisting of the following:

N'-(mercaptoeth-1-yl)-N'-(5-mercapto-3-aza-2-oxopent-1-yl)-N-{5-chloro-2-[2-[4-(4-fluorobenzyl)-2(2R)-methylpiperazin-1-yl]-2-oxoethoxy]phen-1-yl}glycylglycinamide, technetium-99m-complex;

N'(2-(mercaptoeth-1-yl)-N'-(5-mercapto-3-aza-2-oxopent-1-yl)-N-{5-chloro-2-[2-[4-(4-fluorobenzyl)-2-(2R)-methylpiperazin-1-yl]-2-oxoethoxy]phen-1-yl}glycinamide, technetium-99m-complex;

N'-(2-(mercaptoeth-1-yl)-N'-(5-mercapto-3-azapent-1-yl)-N-{5-chloro-2-[2-[4-(4-fluorobenzyl)-2-(2R)-methylpiperazin-1-yl]-2-oxoethoxy]phen-1-yl}glycinamide, technetium-99m-complex, and mono-and dichloride salts thereof.

* * * * *

UNITED STATES PATENT AND TRADEMARK OFFICE
CERTIFICATE OF CORRECTION

PATENT NO. : 6,872,381 B1
APPLICATION NO. : 10/626725
DATED : March 29, 2005
INVENTOR(S) : Christoph-Stephan Hilger et al.

It is certified that error appears in the above-identified patent and that said Letters Patent is hereby corrected as shown below:

Column 32, line 28, reads "to of formula" should read -- to formula --
Column 32, line 46, reads "alkylcarbonylanmino," should read -- alkylcarbonylamino, --
Column 32, line 59, reads "salt thereof, and" should read -- salt thereof; and --
Column 33, line 29, reads "position emission" should read -- positron emission --
Column 33, line 33, reads "reseptor CCR1" should read -- receptor CCR1 --
Column 34, line 11, reads "the reminder of" should read -- the remainder of --
Column 34, line 14, reads "the reminder of" should read -- the remainder of --
Column 34, line 17, reads "-C(O)-CH$_2$N(H)" should read -- -C(O)-CH$_2$-N(H) --
Column 34, line 34, insert line break after "and"
Column 34, line 47, reads "alkyl portion" should read -- alkyl portions --
Column 34, line 59, reads "-N(R$_a$)-C(O)-NH$_2$-N(H)-C(O)-N(H)R$_b$," should read
    -- -N(R$_a$)-C(O)-NH$_2$, -N(H)-C(O)-N(H)R$_b$, --
Column 35, line 5, reads "carbon atoms, and" should read -- carbon atoms; and --
Column 35, line 19, reads "reminder of" should read -- remainder of --
Column 35, line 21, reads "-C(O)-groups," should read -- -C(O)- groups, --
Column 35, line 22, reads "-C(O)N(R)-groups," should read -- -C(O)N(R)- groups, --
Column 35, line 23, reads "-N(R)-groups," should read -- -N(R)- groups, --
Column 35, line 23, reads "-N(R)$_2$" should read -- -N(R)$_2$- --
Column 35, line 30, reads "reminder of" should read -- remainder of --
Column 35, line 32, reads "-C(O)-groups," should read -- -C(O)- groups, --
Column 35, line 33, reads "-C(O)N(R)-groups," should read -- -C(O)N(R)- groups, --
Column 35, line 34, reads "-N(R)-groups," should read -- -N(R)- groups, --
Column 35, line 34, reads "-N(R)$_2$" should read -- -N(R)$_2$- --
Column 35, line 41, reads "reminder of" should read -- remainder of --
Column 35, line 43, reads "-C(O)-groups," should read -- -C(O)- groups, --
Column 35, line 44, reads "-C(O)N(R)-groups," should read -- -C(O)N(R)- groups, --
Column 35, line 45, reads "-N(R)-groups," should read -- -N(R)- groups, --
Column 35, line 45, reads "-N(R)$_2$" should read -- -N(R)$_2$- --
Column 35, line 47, reads "one to ton oxygen" should read -- one to ten oxygen --
Column 35, line 47, reads "one to ton sulfur" should read -- one to ten sulfur --
Column 36, line 1, reads "(2RS,5RS)" should read -- (2SR,5RS) --
Column 36, line 3, reads "(2SR,5SR)" should read -- (2RS,5RS) --
Column 36, line 5, reads "(2RS,5SR)" should read -- (2SR,5SR) --
Column 36, line 34, reads "(2SR,5RS)" should read -- (2RS,5RS) --
Column 36, line 36, reads "{2[(2SR,5SR)" should read -- {2-[(2SR,5RS) --

UNITED STATES PATENT AND TRADEMARK OFFICE
CERTIFICATE OF CORRECTION

PATENT NO.         : 6,872,381 B1
APPLICATION NO.    : 10/626725
DATED              : March 29, 2005
INVENTOR(S)        : Christoph-Stephan Hilger et al.

It is certified that error appears in the above-identified patent and that said Letters Patent is hereby corrected as shown below:

Column 36, line 36, reads "benzyl) 2,5-" should read -- benzyl)-2,5- --
Column 36, line 39, reads "(2RS,5RS)" should read -- (2SR,5SR) --
Column 36, line 43, reads "benzyl)2,5-" should read -- benzyl)-2,5- --
Column 36, line 45, reads "benzyl])" should read -- benzyl) --
Column 36, line 48, reads "(2SR,5RS)" should read -- (2RS,5RS) --
Column 36, line 51, reads "(2SR,5RS)" should read -- (2SR,5SR) --
Column 36, between lines 53 and 54, insert
    -- 1-[(2RS,5SR)-4-(4-fluoro-$^{18}F$-benzyl)-2,5-dimethylpiperazin-1-yl]-2-(2-isopentylamino-4-chlorophenoxy)ethan-1-one; --
Column 36, line 57, reads "(2SR,5RS)" should read -- (2RS,5RS) --
Column 36, line 59, reads "(2SR,5RS)" should read -- (2SR,5SR) --
Column 36, between lines 62 and 63, insert
    -- N-(5-chloro-2-{2-[2RS,5SR)-4-(4-fluoro-$^{18}F$-benzyl)-2,5-dimethylpiperazin-1-yl]-2-oxoethoxy}phenyl)-2-methylpropanamide; --
Column 36, line 64, reads "acetamide" should read -- acetamide; --
Column 36, line 65, reads "(2SR,5RS)" should read -- (2RS,5RS) --
Column 36, line 67, reads "acetamide" should read -- acetamide; --
Column 37, line 1, reads "(2SR,5RS)" should read -- (2SR,5SR) --
Column 37, line 3, reads "acetamide" should read -- acetamide; --
Column 37, line 13, reads "dimethylpiperazin 1-yl" should read
    -- dimethylpiperzin-1-yl --
Column 37, line 15, reads "benzyl)" should read -- benzyl)- --
Column 37, line 27, reads ""dimethylpiperazin 1-yl" should read
    -- dimethylpiperzin-1-yl --
Column 37, line 30, reads ""dimethylpiperazin 1-yl" should read
    -- dimethylpiperzin-1-yl --
Column 37, line 48, reads "{2[(2SR" should read -- {2-[(2SR --
Column 37, line 49, reads "dimethylpiperazin-yl" should read
    -- dimethylpiperazin-1-yl --
Column 37, line 51, reads "{2[(2SR,5RS)" should read -- {2-[(2RS,5RS) --
Column 37, line 52, reads "dimethylpiperazin-yl" should read
    -- dimethylpiperazin-1-yl --
Column 37, line 54, reads "{2[(2SR,5RS)" should read -- {2-[(2SR,5SR) --
Column 37, line 55, reads "dimethylpiperazin-yl" should read
    -- dimethylpiperazin-1-yl --

UNITED STATES PATENT AND TRADEMARK OFFICE
CERTIFICATE OF CORRECTION

PATENT NO. : 6,872,381 B1
APPLICATION NO. : 10/626725
DATED : March 29, 2005
INVENTOR(S) : Christoph-Stephan Hilger et al.

It is certified that error appears in the above-identified patent and that said Letters Patent is hereby corrected as shown below:

Column 37, line 57, reads "{2[(2SR,5RS)" should read -- {2-[(2RS,5SR) --
Column 37, line 58, reads "dimethylpiperazin-yl" should read
    -- dimethylpiperazin-1-yl --
Column 37, line 59, reads "{2[(2SR,5RS)" should read -- {2-[(2SR,5RS) --
Column 37, line 60, reads "dimethylpiperazin-yl" should read
    -- dimethylpiperazin-1-yl --
Column 37, line 62, reads "{2[(2SR,5RS)" should read -- {2-[(2RS,5RS) --
Column 37, line 63, reads "dimethylpiperazin-yl" should read
    -- dimethylpiperazin-1-yl --
Column 37, line 65, reads "{2[(2SR,5RS)" should read -- {2-[(2SR,5SR) --
Column 37, line 66, reads "dimethylpiperazin-yl" should read
    -- dimethylpiperazin-1-yl --
Column 38, line 1, reads "{2[(2SR,5RS)" should read -- {2-[(2RS,5SR) --
Column 38, line 2, reads "dimethylpiperazin-yl" should read
    -- dimethylpiperazin-1-yl --
Column 38, line 7, reads "(2SR,5RS)" should read -- (2RS,5RS) --
Column 38, line 9, reads "(2SR,5RS)" should read -- (2SR,5SR) --
Column 38, line 12, reads "(2SR,5RS)" should read -- (2RS,5SR) --
Column 38, line 14, reads "(2SR,5RS)" should read -- (2RS,5SR) --
Column 38, line 17, reads "(2SR,5RS)" should read -- (2SR,5SR) --
Column 38, line 20, reads "(2SR,5RS)" should read -- (2RS,5RS) --
Column 38, line 31, reads "(2RS,5RS)" should read -- (2SR,5SR) --
Column 38, line 62, reads "(2RS,5SR)" should read -- (2SR,5RS) --
Column 39, line 6, reads "{2 [(2S)" should read -- {2-[(2S) --
Column 39, line 6, reads "-2,5-" should read -- -2- --
Column 39, line 10, reads "(2RS,5SR)" should read -- (2SR,5SR) --
Column 39, line 13, reads "(2RS,5SR)" should read -- (2RS,5RS) --
Column 39, line 16, reads "(2SR,5RS)" should read -- (2RS,5RS) --
Column 39, line 22, reads "(2SR,5RS)" should read -- (2RS,5RS) --
Column 39, line 25, reads "(2SR,5RS)" should read -- (2SR,5SR) --
Column 39, line 28, reads "(2SR,5RS)" should read -- (2RS,5RS) --
Column 39, line 33, reads "(2RS,5SR)" should read -- (2SR,5SR) --
Column 39, line 36, reads "(2RS,5SR)" should read -- (2RS,5RS) --
Column 39, line 39, reads "(2RS,5SR)" should read -- (2SR,5RS) --
Column 39, line 45, reads "(2RS,5SR)" should read -- (2SR,5SR) --

UNITED STATES PATENT AND TRADEMARK OFFICE
CERTIFICATE OF CORRECTION

PATENT NO. : 6,872,381 B1
APPLICATION NO. : 10/626725
DATED : March 29, 2005
INVENTOR(S) : Christoph-Stephan Hilger et al.

It is certified that error appears in the above-identified patent and that said Letters Patent is hereby corrected as shown below:

Column 39, line 48, reads "(2RS,5SR)" should read -- (2RS,5RS) --
Column 39, line 51, reads "(2RS,5SR)" should read -- (2SR,5RS) --
Column 39, line 59, reads "(2SR)" should read -- (2RS) --
Column 39, line 62, reads "(2RS,5SR)" should read -- (2SR,5SR) --
Column 39, line 65, reads "(2SR)" should read -- (2RS) --
Column 39, line 65, reads "(2RS,5SR)" should read -- (2RS,5RS) --
Column 40, line 1, reads "(2RS,5SR)" should read -- (2RS,5RS) --
Column 40, line 37, reads "(2SR,5RS)" should read -- (2RS,5RS) --
Column 40, line 40, reads "(2SR,5RS)" should read -- (2SR,5SR) --
Column 40, line 43, reads "(2SR,5RS)" should read -- (2RS,5SR) --
Column 40, line 47, reads "(2R)" should read -- (2S) --
Column 40, line 54, reads "2(2R)" should read -- 2-(2R) --
Column 40, line 57, reads "N'(2-(mercaptoeth" should read -- N'-(2-mercaptoeth --
Column 40, line 61, reads "N'-(2-(mercaptoeth" should read -- N'-(2-mercaptoeth --
Column 40, line 65, reads "mono-and" should read -- mono- and --

Signed and Sealed this

Twenty-second Day of December, 2009

David J. Kappos
*Director of the United States Patent and Trademark Office*